United States Patent
Ishiwata et al.

(10) Patent No.: US 6,448,242 B1
(45) Date of Patent: Sep. 10, 2002

(54) CYCLIC AMIDE COMPOUNDS

(75) Inventors: Hiroyuki Ishiwata, Ichikawa; Seiichi Sato, Tokyo; Mototsugu Kabeya; Soichi Oda, both of Higashimurayama; Yukio Hattori, Ushiku; Makoto Suda; Manabu Shibasaki, both of Tsukuba; Hiroshi Nakao; Takao Nagoya, both of Tsuchiura, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/622,586

(22) PCT Filed: Feb. 16, 1999

(86) PCT No.: PCT/JP99/00659

§ 371 (c)(1), (2), (4) Date: Aug. 21, 2000

(87) PCT Pub. No.: WO99/42446

PCT Pub. Date: Aug. 26, 1999

(30) Foreign Application Priority Data

Feb. 19, 1998 (JP) .............................. 10-37650

(51) Int. Cl.⁷ .............................. A07N 43/00
(52) U.S. Cl. ............. 514/210.18; 514/218; 514/252.02; 514/252.11; 514/255.05; 514/256; 514/385; 514/252.12; 514/403; 540/470; 540/480; 540/481; 540/575; 540/553; 544/295; 544/357; 544/239; 544/296; 544/298; 544/322; 544/333
(58) Field of Search .............................. 544/239, 296, 544/298, 322, 333, 295, 357; 514/2, 252.02, 252.12, 256, 210.18, 218, 252.11, 255.05, 385, 403; 540/470, 480, 481, 575, 553

(56) References Cited

FOREIGN PATENT DOCUMENTS

| EP | 0 787 491 | 8/1997 |
|----|-----------|--------|
| JP | 1-106818 | 4/1989 |
| JP | 7-17506 | 3/1995 |
| JP | 8-92216 | 4/1996 |
| JP | 8-109177 | 4/1996 |

OTHER PUBLICATIONS

Ponasik, Chemical Abstracts 124:80349, 1995, abstract of Biochem J, vol. 311(2), pp 371–5.*

N. Matsuura, et al., Jpn Pharmacol Ther, vol. 22, No. 3, pp. 1369–1383, "An Immunopharmacological Study of ($\pm$)–[2–[4–(3–Ethoxy–2–Hydroxypropoxy) Phenylcarbamoyl] Ethyl]Dimethylsulfonium p–Toluenesulfonate (Suplatast Tosilate, IPD–1151T)", 1994.

\* cited by examiner

Primary Examiner—D. Margaret Seaman
(74) Attorney, Agent, or Firm—Oblon, Spivak, McClelland, Maier & Neustadt, P.C.

(57) ABSTRACT

The invention relates to compounds represented by the following general formula (1):

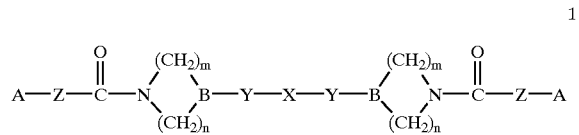

wherein A is an aromatic compound which may be substituted, or the like, B is a nitrogen atom or CH, X is a lower alkylene group which may be substituted, or the like, Y is a single bond or the like; Z is a divalent residue of benzene which may be substituted, or the like, and m and n are independently an integer of 1 to 4, and medicines comprising such a compound. These compounds have an excellent inhibitory effect on the production of an IgE antibody and are hence useful as antiallergic agents and the like.

23 Claims, No Drawings

CYCLIC AMIDE COMPOUNDS

This application is a 371 of PCT/JP99/00659, filed Feb. 16, 1999.

TECHNICAL FIELD

The present invention relates to novel cyclic amide compounds and medicines useful in preventing and treating allergic immunological diseases or the like, comprising such a compound as an active ingredient.

BACKGROUND ART

IgE, which is a kind of immunoglobulin (Ig), is an allergen-specific molecule produced by an IgE producing cell differentiated from a B cell. This process is triggered by the contact of an immunocyte with an allergen in vivo.

IgE is produced in a target organ for an allergy and binds to a receptor on the surface of a mast cell, which is a central effector cell in an allergic reaction, or a basophil (sensitized state). After the sensitization, allergic chemical mediators such as histamine, leukotrienes, prostaglandins and PAF, and injuring enzymes such as tryptase are released from the mast cell stimulated by the reaction of the specific IgE and an allergen which invades in the living body, so that immediate responses such as vascular permeability acceleration, smooth muscle constriction and vasodilation are elicited. Further, cytokines such as IL-4, which directly activate other immune system cells, are also secreted from the stimulated mast cell. As a result, eosinophils, basophils and the like infiltrate into a tissue, and the allergic chemical mediators and tissue injuring proteins such as MBP, which are secreted by these inflammatory cells, induce a late response, so that the allergic symptom is lingered and taken seriously ill.

From this, IgE is considered a substance fundamentally participating in the attack of an allergic immunological disease.

Therefore, several compounds having an inhibitory effect on the production of an IgE antibody have heretofore been found and reported with a view toward developing antiallergic agents [Pharmacology and Therapy, 1994, 22(3), 1369; Japanese Patent Application Laid-Open No. 106818/1989; Japanese Patent Publication No. 17506/1995; Japanese Patent Application Laid-Open Nos. 92216/1996 and 109177/1996; and WO 96/11682]. However, the object has been not always sufficiently achieved under the circumstances.

Accordingly, it is an object of the present invention to find a compound having a strong inhibitory effect on the production of an IgE antibody so as to provide a medicine effective for allergic immunological diseases, comprising this compound as an active ingredient.

DISCLOSURE OF THE INVENTION

With the foregoing circumstances in view, the present inventors have carried out an extensive investigation. As a result, it has been found that novel cyclic amide compounds represented by the general formula (1), which will be described subsequently, salts thereof, or solvates thereof have an excellent inhibitory effect on the production of an IgE antibody and are useful as medicines such as antiallergic agents, thus leading to completion of the present invention.

According to the present invention, there is thus provided a compound represented by the following general formula (1):

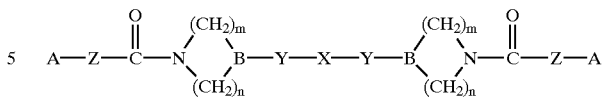

wherein A is a residue of an alicyclic compound which may be substituted, an aromatic compound which may be substituted, or a heterocyclic compound which may be substituted;

X is a single bond; a lower alkylene group which may be substituted; a divalent residue of an alicyclic compound which may be substituted, an aromatic compound which may be substituted, or a heterocyclic compound which may be substituted; an imino group which may be substituted; or a sulfur atom or an oxygen atom;

Y is a single bond, or a lower alkylene, imino or lower alkylimino group;

Z is a group of —CH=CH—, —C≡C—, —(CH=CH)$_2$—, —C≡C—CH=CH— or —CH=CH—C≡C—, or a divalent residue of benzene, pyridine, pyrimidine or pyrazine which may be substituted;

B is a nitrogen atom or =CH—; and m and n are the same or different from each other and independently an integer of b 1to 4 a salt thereof, or a solvate thereof.

According to the present invention, there is also provided a medicine comprising the above compound (1) as an active ingredient.

According to the present invention, there is further provided a medicinal composition comprising the above compound (1) and a pharmaceutically acceptable carrier.

According to the present invention, there is still further provided use of the above compound (1) for a medicine.

According to the present invention, there is yet still further provided a method of treating an allergic immunological disease, which comprises administering the above compound (1).

BEST MODE FOR CARRYING OUT THE INVENTION

In the present invention, examples of the alicyclic compound represented by A or X include saturated or unsaturated alicyclic compounds having 3 to 14 carbon atoms, for example, cycloalkanes such as cyclopropane, cyclobutane, cyclopentane, cyclohexane, cycloheptane and cyclooctane; cycloalkenes such as cyclopentene and cyclohexene; and bicyclic fused cycloalkenes such as indene, indane, dihydronaphthalene and tetrahydronaphthalene.

Examples of the aromatic compound include aromatic compounds having 5 to 14 carbon atoms, such as benzene and naphthalene.

Examples of the heterocyclic compound include 5- to 7-membered heterocyclic compounds containing 1 to 3 nitrogen atoms, such as pyrrolidine, pyridine, piperidine, piperazine and homopiperazine.

Examples of the lower alkylene group represented by X or Y include linear or branched alkylene groups having 1 to 8 carbon atoms, and specifically, methylene, ethylene, propylene, trimethylene, tetramethylene, pentamethylene, hexamethylene, heptamethylene and octamethylene groups.

In the formula (1), it is particularly preferred that A be a phenyl, naphthyl, dihydronaphthyl, indenyl, pyridyl, indolyl, isoindolyl, quinolyl or isoquinolyl group. These groups may have 1 to 3 substituents. Here, examples of the substituents on these groups include a hydroxyl group, halogen atoms, lower alkyl groups which may be substituted by 1 to 3 halogen atoms, lower alkoxy groups, an amino group, monoalkylamino groups, dialkylamino groups, and lower alkylthio groups. As A, a phenyl group substituted by 1 to 3 substituents selected from among lower alkyl groups and lower alkoxy groups is particularly preferred.

The lower alkylene group represented by X is preferably a linear or branched alkylene group having 1 to 8 carbon atoms. A linear alkylene group having 2 to 4 carbon atoms is more preferred. These groups may have substituents such as halogen atoms, or hydroxyl, lower alkoxy, amino, monoalkylamino, dialkylamino, carboxyl or lower alkoxycarbonyl groups. Of these, a lower alkylene group which may be substituted by an amino, monoalkylamino, dialkylamino, carboxyl or lower alkoxycarbonyl group is particularly preferred.

The divalent residue of the alicyclic compound, which is represented by X, is preferably a divalent residue of a cycloalkane having 5 to 8 carbon atoms. Examples of the divalent residue of the aromatic compound, which is represented by X, include phenylene and naphthylene groups, with the phenylene group being particularly preferred. Here, the phenylene group may be any of 1,2-phenylene, 1,3-phenylene and 1,4-phenylene groups, with the 1,2-phenylene or 1,4-phenylene group being particularly preferred. Preferable examples of the divalent residue of the heterocyclic compound, which is represented by X, include divalent residues of pyridine, pyrrolidine, piperidine, piperazine and homopiperazine. The divalent residue of the alicyclic compound, aromatic compound or heterocyclic compound, or the imino group, which is represented by X, may be substituted by a halogen atom, a hydroxyl group, a lower alkyl group which may be substituted by an amino, monoalkylamino or dialkylamino group, a lower alkoxy group, a carboxyl group, a lower alkoxycarbonyl group, an amino group, an alkylamino group, a dialkylamino group, a nitro group, a cyano group, an aralkyl group, or the like. Here, examples of the alkylamino and dialkylamino groups include lower alkylamino groups and di-lower alkylamino groups, respectively.

It is preferred that X be the alkylene group having 1 to 8 carbon atoms, the divalent residue of the aromatic compound which may be substituted, or the divalent residue of the heterocyclic compound which may be substituted.

Y is preferably a single bond or an alkylene group having 1 to 8 carbon atoms.

Examples of groups which may be substituted on the divalent residue of benzene, pyridine, pyrimidine or pyrazine represented by Z include halogen atoms, and lower alkyl, lower alkoxy, amino and nitro groups. Z is preferably a divalent residue of benzene which may be substituted.

The group $-N\underset{(CH_2)_n}{\overset{(CH_2)_m}{\diagup\diagdown}}B-$ is particularly preferably a 1,4-piperazinyl, 1,4-homopiperazinyl or 1,4-piperidinyl group.

In the above-described various substituent groups or the like, "alkyl" in the alkyl groups, alkylamino groups, dialkylamino groups, alkylthio groups and the like generally includes linear or branched alkyl having 1 to 12 carbon atoms. Of these, lower alkyl groups are preferred. The lower alkyl groups include linear or branched alkyl groups having 1 to 8 carbon atoms. Specific examples thereof include methyl, ethyl, n-propyl, isopropyl, n-butyl, isobutyl, sec-butyl, tert-butyl, pentyl, hexyl, heptyl and octyl groups. Of these, those having 1 to 6 carbon atoms, for example, methyl, ethyl, n-propyl, isopropyl, n-butyl, isobutyl, sec-butyl, tert-butyl, n-pentyl and n-hexyl groups, are particularly preferred.

"Alkoxy" in the alkoxy groups, alkoxycarbonyl groups and the like generally includes linear or branched alkoxy having 1 to 12 carbon atoms. Of these, lower alkoxy groups are preferred. The lower alkoxy groups include linear or branched alkoxy groups having 1 to 8 carbon atoms. Specific examples thereof include methoxy, ethoxy, n-propoxy, isopropoxy, n-butoxy, isobutoxy, sec-butoxy, tert-butoxy, pentyloxy, hexyloxy, heptyloxy and octyloxy groups. Of these alkoxy groups, those having 1 to 6 carbon atoms are preferred.

Examples of the aralkyl group include $C_{6-14}$-aryl-$C_{1-8}$-alkyl groups such as benzyl, phenylethyl and naphthylmethyl groups.

Examples of the lower alkylthio group include alkylthio groups having 1 to 8 carbon atoms.

The halogen atoms include fluorine, chlorine, bromine and iodine atoms.

No particular limitation is imposed on the salts of the cyclic amide compounds (1) according to the present invention so far as they are pharmaceutically acceptable salts. In the case where the cyclic amide compounds (1) are basic compounds, however, examples of the salts include mineral acid salts such as hydrochlorides, sulfates and nitrates; and organic acid salts such as methanesulfonates, acetates, oxalates and citrates. In the case where the cyclic amide compounds (1) are acidic compounds on the other hand, examples of the salts include alkali metal salts such as sodium salts and potassium salts; alkaline earth metal salts such as calcium salts and magnesium salts; and organic base salts such as pyridine salts, picoline salts and triethylamine salts.

The cyclic amide compounds (1) may be present in the form of solvates such as hydrates.

The cyclic amide compounds (1) according to the present invention can be prepared according to, for example, the following reaction formula:

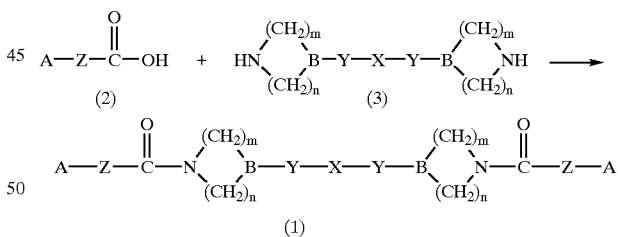

wherein A, X, Y, Z, B, m and n have the same meanings as defined above.

More specifically, the compounds (1) according to the present invention are obtained by the N-acylating reaction of a carboxylic acid (2) with a diamine (3).

The N-acylating reaction may be conducted by using any N-acylating reaction known per se in the art. It is preferable to apply, for example, (a) a method in which the carboxylic acid (2) and the diamine (3) are reacted in the presence of a condensation reagent, preferably, in the presence of a condensation reagent and a base, in a solvent, or (b) a method in which a reactive derivative of the carboxylic acid and the diamine (3) are reacted in a solvent, preferably, in the presence of a base.

Examples of the solvents used in these reactions may include dimethylformamide, tetrahydrofuran, dioxane, acetonitrile, methylene chloride and dichloroethane. As the base, may be used an organic base such as pyridine, triethylamine or diisopropylethylamine, or an inorganic base such as sodium carbonate or sodium hydrogencarbonate. Examples of usable condensation reagents include 1,3-dicyclohexylcarbodiimide, 1-cyclohexyl-3-morpholinoethyl-carbodiimide, 1-(3-dimethylaminopropyl)-3-ethylcarbodiimide, 1,1'-carbonyldiimidazole, diethyl phosphorocyanidate, diphenylphosphoryl azide, bis(2-oxo-3-oxazolidinyl)-phosphinic chloride and 2-chloro-1-methylpyridinium iodide. Examples of usable derivatives of the carboxylic acid include acid halides such as acid chlorides, acid azides, symmetric acid anhydrides, mixed anhydrides with pivalic acid or the like, and active esters such as cyanomethyl esters and p-nitrophenyl esters.

In each of the method (a) and the method (b), the N-acylating reaction is completed by reacting the carboxylic acid (2) or the reactive derivative thereof with the diamine (3) at a reaction temperature of 0° C. to 100° C. for 30 minutes to 30 hours. The isolation and purification of the compound (1) from the reaction mixture may be conducted by using any methods known per se in the art, for example, filtration, extraction, washing, drying, concentration, recrystallization and various kinds of chromatography.

The compound (1) thus obtained may be converted into an acid-addition salt or a base salt in a method known per se in the art.

The compound (1) may also be converted into a solvate with a reaction solvent, solvent for recrystallization, or the like, in particular, a hydrate.

Since the cyclic amide compounds (1) according to the present invention have an excellent inhibitory effect on the production of an IgE antibody as demonstrated in Test Example, which will be described subsequently, and inhibitory effects on the production of IL-4 and IL-5, they are useful as medicines for prevention and treatment of various allergic immunological diseases, for example, asthma, atopic dermatitis, allergic rhinitis, inflammatory bowel disease, contact dermatitis, allergic ophthalmopathy and the like.

The cyclic amide compounds (1) or the salts thereof according to the present invention can be formulated into medicinal composition, for example, various oral and parenteral preparations in the form of a solid, semisolid or liquid by adding a pharmaceutically acceptable, inorganic or organic carrier in accordance with a method known per se in the art.

Examples of the oral preparations include tablets, pills, granules, soft and hard capsules, powders, grains, triturations, emulsions, syrups, pellets and elixirs. Examples of the parenteral preparations include injections, drops, infusions, ointments, lotions, tonics, sprays, suspensions, oils, emulsions, suppositories and eye drops.

The active ingredients according to the present invention may be formulated into various preparations in accordance with a method known per se in the art. In these preparations, may be suitably used surfactants, excipients, colorants, smell corrigents, preservatives, stabilizers, buffers, suspension stabilizers, isotonic agents and the like, as needed.

The dose of the cyclic amide compound (1) or the salt thereof varies according to the kind of the compound, the kind of a disease to be treated or prevented, an administration method, the age, sex and weight of a patient to be administered, treatment time, and the like. However, the compound may be administered in a dose of 0.01 to 1,000 mg/kg of weight/day. The compound may be administered at once or in several portions, for example, 2 to 6 portions a day.

EXAMPLES

The present invention will hereinafter be described in more detail by the following Examples. However, the present invention is not limited to these examples.

Referential Example 1

Preparation of 1,3-bis(1-piperazinyl)propane tetrahydrochloride[1]

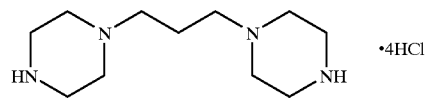

1,3-Dibromopropane (1.0 ml; 9.9 mmol) and potassium carbonate (2.0 g; 15 mmol) were added to a solution of 1-formylpiperazine (2.5 g; 22 mmol) in dimethylformamide (5 ml), and the mixture was stirred for 20 hours in a bath controlled at 60° C. Water was added to the reaction mixture to conduct extraction with chloroform. The organic layer was washed with saturated brine, dried over anhydrous sodium sulfate and then concentrated under reduced pressure. The resultant crude oil was purified by column chromatography on silica gel, thereby obtaining 2.13 g (yield: 81%) of 1,3-bis(4-formyl-1-piperazinyl)propane as a colorless oil.

Concentrated hydrochloric acid (6.0 ml; 72 mmol) was added to a solution in methanol (18 ml) of 1,3-bis(4-formyl-1-piperazinyl)propane (950 mg; 3.5 mmol) synthesized by the above process, and the mixture was stirred for 6 hours in a bath controlled at 65° C. The reaction mixture was concentrated under reduced pressure, and the resultant crude crystals were washed with ethanol and diethyl ether, thereby obtaining 960 mg (yield: 76%) of the title compound as a colorless crystalline powder [melting point: 260° C. (decomposition)].

(1) GB 840358 1957.

Referential Example 2

Preferation of 1,4-bis(1-piperazinyl)benzene

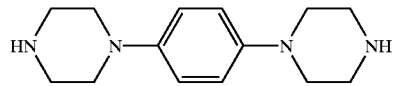

1-Benzylpiperazine (2.8 ml; 16 mmol) and potassium carbonate (2.3 g; 17 mmol) were added to a solution of 1-chloro-4-nitrobenzene (2.0 g; 13 mmol) in dimethylformamide (0.5 ml), and the mixture was stirred for 7 hours in a bath controlled at 100° C. Water was added to the reaction mixture to conduct extraction with chloroform. The organic layer was washed with saturated brine, dried over anhydrous sodium sulfate and then concentrated under reduced pressure. The resultant crude oil was purified by column chromatography on silica gel, thereby obtaining 2.9 g (yield: 76%) of 4-(4-benzyl-1-piperazinyl)-1-nitrobenzene as a colorless oil.

4-(4-Benzyl-1-piperazinyl)-1-nitrobenzene (2.6 g; 8.9 mmol) synthesized by the above process and zinc powder (3.2 g; 48 mmol) were added to a solution of calcium chloride (665 mg; 6.0 mmol) in water-ethanol-acetic acid (12 ml-55 ml-1.2 ml), and the mixture was stirred under reflux for 15 minutes in a bath controlled at 110° C. Insoluble substances were removed from the reaction mixture by suction filtration through Celite, and the filtrate was concentrated under reduced pressure. A saturated aqueous solution of sodium hydrogencarbonate was added to the resultant concentrated residue to conduct extraction with chloroform. The organic layer was dried over anhydrous sodium sulfate and then concentrated under reduced pressure. The thus-obtained crude crystals were recrystallized from benzene-n-hexane to obtain 2.3 g (yield: 96%) of 4-(4-benzyl-1-piperazinyl)aniline as pale brown needles (melting point: 137–138° C.).

Bis(2-chloroethyl)amine hydrochloride (534 mg; 3.0 mmol) and sodium iodide (3.0 g; 20 mmol) were added to a solution in methanol (20 ml) of 4-(4-benzyl-1-piperazinyl)-aniline (1.1 g; 4.1 mmol) synthesized by the above process, and the mixture was stirred for 13 hours in a bath controlled at 70° C. The reaction mixture was concentrated under reduced pressure, and a 5% aqueous solution of sodium hydrogencarbonate was added to the resultant concentrated residue to conduct extraction with chloroform. The organic layer was washed with saturated brine, dried over anhydrous sodium sulfate and then concentrated under reduced pressure. The resultant crude oil was purified by column chromatography on silica gel, thereby obtaining 775 mg of impurity-containing 4-(4-benzyl-1-piperazinyl)-1-(1piperazinyl)benzene as an oil. Trimethylamine (0.3 ml; 2.2 mmol) and di-tert-butyl dicarbonate (450 mg; 2.1 mmol) were added to a solution of this oil (775 mg) in methylene chloride (5 ml) under ice cooling, and the mixture was stirred for 30 minutes. A saturated aqueous solution of sodium hydrogencarbonate was added to the reaction mixture to conduct extraction with chloroform. The organic layer was washed with saturated brine, dried over anhydrous sodium sulfate and then concentrated under reduced pressure. The resultant crude oil was purified by column chromatography on silica gel, thereby obtaining crude crystals (738 mg; yield: 42%) of 4-(4-benzyl-1-piperazinyl)-1-(4-tert-butoxycarbonyl-1-piperazinyl)-benzene. The crude crystals were recrystallized from chloroform-diethyl ether-n-hexane to obtain colorless flakes (melting point: 132–133° C.).

10% Palladium on carbon (104 mg) and concentrated hydrochloric acid (0.60 ml; 7.2 mmol) were added to a solution in methanol (10 ml) of 4-(4-benzyl-1-piperazinyl)-1-(4-tert-butoxycarbonyl-1-piperazinyl)benzene (354 mg; 0.81 mmol) synthesized by the above process. After the mixture was stirred for 12 hours in a bath controlled at 55° C. under hydrogen, the catalyst was removed from the reaction mixture by filtration. After the filtrate was concentrated under reduced pressure, a process of adding ethanol (10 ml) to the residue and concentrating the mixture under reduced pressure was conducted twice. The resultant concentrated residue was dissolved in water (5 ml), and potassium carbonate (400 mg; 2.9 mmol) and di-tert-butyl dicarbonate (1.0 g; 4.6 mmol) were added to this solution under ice cooling. After the mixture was stirred for 30 minutes, the reaction mixture was extracted with chloroform. The organic layer was washed with saturated brine, dried over anhydrous sodium sulfate and then concentrated under reduced pressure. The resultant crude oil was purified by column chromatography on silica gel, thereby obtaining 1,4-bis(4-tert-butoxycarbonyl-1-piperazinyl)benzene (59 mg; yield: 16%) as a colorless oil.

Trifluoroacetic acid (1 ml) was added to a solution in methylene chloride (1 ml) of 1,4-bis(4-tert-butoxycarbonyl-1-piperazinyl)benzene (59 mg; 0.13 mmol) synthesized by the above process under ice cooling, and the mixture was stirred for 30 minutes. The reaction mixture was then concentrated under reduced pressure, and the resultant concentrated residue (81 mg) was dissolved in methanol-chloroform (1:2). The solution was applied to a column packed with alumina (3 g), and the column was eluted with methanol-chloroform (1:2). The eluate was concentrated under reduced pressure, thereby obtaining 31 mg (yield: 88%) of the title compound as a colorless oil.

Referential Example 3

Preparation of methyl 2,2-bis[(4-piperidinyl)-methyl]acetate dihydrochloride

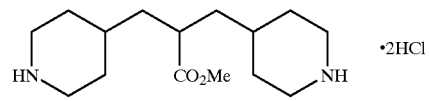

A 50% dispersion of sodium hydride in a mineral oil (6.6 g; 140 mmol) was added to a solution of di-tert-butyl malonate (10 g; 46 mmol) in dimethylformamide (100 ml) under ice cooling, and the mixture was stirred for 30 minutes. (4-Chloromethyl)pyridine (11.6 g; 90 mmol) was then added to this solution, and the mixture was stirred for 30 minutes in a bath controlled at 70° C. The reaction mixture was poured into ice water and extracted with diethyl ether. The organic layer was washed with water and saturated brine, dried over anhydrous sodium sulfate and then concentrated under reduced pressure, thereby obtaining crude crystals (17.1 g) of di-tert-butyl 2,2-bis[(4-pyridyl)methyl]malonate.

The crude crystals (17.1 g) of di-tert-butyl 2,2- bis[(4-pyridyl)methyl]malonate synthesized by the above process were dissolved in trifluoroacetic acid (90 ml), and the solution was stirred at room temperature for 30 minutes. The reaction mixture was concentrated under reduced pressure, and the resultant concentrated residue was heated for 20 minutes in a bath controlled at 200° C. and then dissolved in methanol (170 ml). A 4N hydrogen chloride in ethyl acetate (100 ml; 400 mmol) was added to the solution, and the mixture was stirred for 2 hours and then concentrated under reduced pressure. The resultant concentrated residue was made basic by addition of aqueous 2.5N sodium hydroxide and extracted with chloroform. The organic layer was washed with saturated brine, dried over anhydrous sodium sulfate and then concentrated under reduced pressure. The resultant crude oil was purified by column chromatography on silica gel, thereby obtaining 6.0 g (yield: 51%) of methyl 2,2-bis[(4-pyridyl)methyl]acetate as a colorless oil.

Platinum oxide (1.2 g) was added to a solution in acetic acid (20 ml) of methyl 2,2-bis[(4-pyridyl)methyl]acetate (1.8 g; 7.1 mmol) synthesized by the above process, and the mixture was stirred for 12 hours in a bath controlled at 70° C. under hydrogen. The catalyst was removed from the reaction mixture by filtration, and the filtrate was concentrated under reduced pressure. The resultant concentrated residue was dissolved in methanol (20 ml. Triethylamine (10 ml; 72 mmol) and di-tert-butyl dicarbonate (8.4 g; 39 mmol) were added to this solution and the mixture was stirred at room temperature for 1 hour. The reaction mixture was concentrated under reduced pressure, and the resultant concentrated residue was dissolved in ethyl acetate. The solution was washed successively with 3N hydrochloric acid, a saturated aqueous solution of sodium hydrogencarbonate and saturated brine, dried over anhydrous sodium sulfate and then concentrated under reduced pressure. The resultant crude oil was purified by column chromatography on silica gel, thereby obtaining 3.1 g (yield: 95%) of methyl 2,2-bis[(1-tert-butoxycarbonyl-4-piperidinyl)methyl]acetate as a colorless oil.

A 4N hydrogen chloride in ethyl acetate (1.0 ml; 4.0 mmol) was added to a solution in ethyl acetate (0.5 ml) of methyl 2,2-bis[(1-tert-butoxycarbonyl-4-piperidinyl)-methyl]acetate (210 mg; 0.45 mmol) synthesized by the above process, and the mixture was stirred at room temperature for 30 minutes and then concentrated under reduced pressure. The concentrated residue was suspended in diethyl ether and collected by filtration to obtain 116 mg (yield: 76%) of the title compound as a colorless crystalline powder (melting point: 269–271° C.).

Referential Example 4

Preparation of 1,3-bis(1-tert-butoxycarbonyl-4-piperidinyl)-2-(dimethylamino)propane

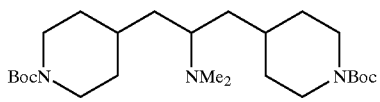

An aqueous 5N sodium hydroxide (5 ml; 25 mmol) was added to a solution in methanol (5 ml) of methyl 2,2-bis[(1-tert-butoxycarbonyl-4-piperidinyl)methyl]acetate (906 mg; 1.9 mmol) synthesized by the process described in Referential Example 3, and the mixture was stirred for 30 minutes in a bath controlled at 100° C. The reaction mixture was made acidic by addition of 6N hydrochloric acid and extracted with chloroform. The organic layer was washed with saturated brine, dried over anhydrous sodium sulfate and then concentrated under reduced pressure. The resultant crude oil was purified by column chromatography on silica gel, thereby obtaining 861 mg (yield: 98%) of 2,2-bis[(1-tert-butoxycarbonyl-4-piperidinyl)methyl]acetic acid as a colorless oil.

Triethylamine (0.39 ml; 2.8 mmol), diphenylphosphoryl azide (0.61 ml; 2.8 mmol) and benzyl alcohol (0.39 ml; 3.8 mmol) were added to a solution in toluene (10 ml) of 2,2-bis[(1-tert-butoxycarbonyl-4-piperidinyl)methyl]acetic acid (850 mg; 1.9 mmol) synthesized by the above process, and the mixture was stirred for 12 hours in a bath controlled at 100° C. The reaction mixture was concentrated under reduced pressure, and the resultant concentrated residue was dissolved in ethyl acetate. This solution was washed successively with a saturated aqueous solution of sodium hydrogencarbonate and saturated brine, dried over anhydrous sodium sulfate and then concentrated under reduced pressure. The resultant crude oil was purified by column chromatography on silica gel, thereby obtaining 639 mg (yield: 61%) of 2-benzyloxycarbonylamino-1,3-bis(1-tert-butoxycarbonyl-4-piperidinyl)propane as a colorless oil.

10% Palladium on carbon (125 mg) was added to a solution in ethanol (10 ml) of 2-benzyloxycarbonylamino-1,3-bis[(1-tert-butoxycarbonyl-4-piperidinyl)propane (639 mg; 1.1 mmol) synthesized by the above process, and the mixture was stirred for 3 hours in a bath controlled at 50° C. under hydrogen. The catalyst was removed from the reaction mixture by filtration, and the filtrate was concentrated under reduced pressure. The resultant crude oil was purified by column chromatography on silica gel, thereby obtaining 403 mg (yield: 83%) of 2-amino-1,3-bis(1-tert-butoxycarbonyl-4-piperidinyl)propane as a colorless oil.

A 37% aqueous solution of formaldehyde (0.75 ml; 10 mmol) and sodium cyanoborohydride (194 mg; 3.0 mmol) were added to a solution in acetonitrile (15 ml) of 2-amino-1,3-bis(1-tert-butoxycarbonyl-4-piperidinyl)propane (373 mg; 0.88 mmol) synthesized by the above process, and the mixture was stirred at room temperature for 30 minutes. Acetic acid was then added to the solution to adjust the pH to about 5, and the mixture was stirred further for 30 minutes at room temperature. The reaction mixture was brought to pH about 10 by addition of aqueous 2.5N sodium hydroxide and extracted with chloroform. The organic layer was washed with saturated brine, dried over anhydrous sodium sulfate and then concentrated under reduced pressure. The resultant crude oil was purified by column chromatography on silica gel, thereby obtaining 388 mg (yield: 98%) of the title compound as a colorless oil.

Referential Example 5

Preparation of 1,3-bis(1-tert-butoxycarbonyl-4-piperidinyl)-2-[(dimethylamino)methyl]propane

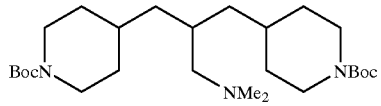

Under ice cooling, calcium chloride (968 mg; 8.8 mmol) and sodium borohydride (668 mg; 17 mmol) were added to a solution in tetrahydrofuran-ethanol (9 ml–14 ml) of methyl 2,2-bis[(1-tert-butoxycarbonyl-4-piperidinyl)-methyl]acetate (1.0 g; 2.1 mmol) synthesized by the process described in Referential Example 3, and the mixture was stirred for 2 hours. The reaction mixture was concentrated under reduced pressure, and the resultant concentrated residue was dissolved in chloroform. The solution was washed successively with 3N hydrochloric acid, a saturated aqueous solution of sodium hydrogencarbonate and saturated brine, dried over anhydrous sodium sulfate and then concentrated under reduced pressure. The resultant crude oil was purified by column chromatography on silica gel, thereby obtaining 900 mg (yield: 96%) of 2,2-bis[(1-tert-butoxycarbonyl-4-piperidinyl)methyl]ethyl alcohol as a colorless oil.

After pyridine (0.090 ml; 1.1 mmol), carbon tetrabromide (716 mg; 2.2 mmol) and triphenylphosphine (567 mg; 2.2 mmol) were added to a solution in diethyl ether (5 ml) of 2,2-bis[(1-tert-butoxycarbonyl-4-piperidinyl)methyl]ethyl alcohol (476 mg; 1.1 mmol) synthesized by the above process under ice cooling, the ice bath was removed, and the mixture was stirred at room temperature for 12 hours. The reaction mixture was filtered, and the filtrate was concentrated under reduced pressure. The resultant crude oil was purified by column chromatography on silica gel, thereby obtaining 465 mg (yield: 86%) of 1,3-bis(1-tert-butoxycarbonyl-4-piperidinyl)-2-(bromomethyl)propane as a colorless oil.

Dimethylamine hydrochloride (638 mg; 7.8 mmol), potassium carbonate (1.2 g; 8.7 mmol) and potassium iodide (144 mg; 0.87 mmol) were added to a solution in dimethylformamide (10 ml) of 1,3-bis(1-tert-butoxycarbonyl-4-piperidinyl)-2-(bromomethyl)propane (437 mg; 0.87 mmol)

synthesized by the above process, and the mixture was stirred for 4 hours in a bath controlled at 60° C. A 0.1N aqueous solution of sodium hydroxide was added to the reaction mixture to conduct extraction with diethyl ether. The organic layer was washed with saturated brine, dried over anhydrous sodium sulfate and then concentrated under reduced pressure. The resultant crude oil was purified by column chromatography on silica gel, thereby obtaining 243 mg (yield: 60%) of the title compound as a colorless oil.

Referential Example 6

Preparation of N,N-bis[(4-piperidinyl)methyl] methyl-amine trihydrochloride

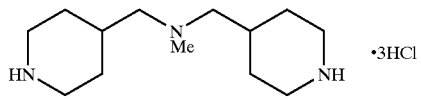

Sodium cyanoborohydride (440 mg; 7.0 mmol) was added to a solution of [(1-tert-butoxy-carbonyl-4-piperidinyl)-methyl]amine (1.5 g; 7.0 mmol) in methanol (30 ml) under ice cooling, and the mixture was stirred for 15 minutes. A solution of 1-tert-butoxycarbonyl-4-piperidine-carbaldehyde (1.4 g; 9.1 mmol) in methanol (5 ml) and acetic acid (0.40 ml; 7.0 mmol) were added to the resultant solution, and the mixture was stirred for 4 hours. After the ice bath was removed, the mixture was stirred at room temperature for 48 hours. The reaction mixture was concentrated under reduced pressure and the resultant concentrated residue was added to a saturated aqueous solution of sodium hydrogencarbonate to conduct extraction with chloroform. The organic layer was washed with saturated brine, dried over anhydrous sodium sulfate and then concentrated under reduced pressure. The resultant crude oil was purified by column chromatography on silica gel, thereby obtaining 1.83 g (yield: 63%) of N,N-bis[(1-tert-butoxycarbonyl-4-piperidinyl)methyl]amine as a colorless oil.

A 37% aqueous solution of formaldehyde (5 ml; 67 mmol) and sodium cyanoborohydride (314 mg; 5.0 mmol) were added to a solution in acetonitrile (20 ml) of N,N-bis[(1-tert-butoxycarbonyl-4-piperidinyl)methyl]amine (1.0 g; 2.4 mmol) synthesized by the above process, and the mixture was stirred at room temperature for 15 minutes. Acetic acid was then added to the solution to adjust the pH to about 5, and the mixture was stirred further for 48 hours at room temperature. The reaction mixture was brought to pH about 10 by addition of aqueous 2.5N sodium hydroxide and extracted with chloroform. The organic layer was washed with saturated brine, dried over anhydrous sodium sulfate and then concentrated under reduced pressure. The resultant crude oil was purified by column chromatography on silica gel, thereby obtaining 989 mg (yield: 95%) of N,N-bis[(1-tert-butoxycarbonyl-4-piperidinyl)methyl]-methylamine as a colorless oil.

After a 4N hydrogen chloride in ethyl acetate (5 ml; 20 mmol) was added to a solution in methylene chloride (3 ml) of N,N-bis[(1-tert-butoxycarbonyl-4-piperidinyl)methyl] methylamine (640 mg; 1.5 mmol) synthesized by the above process under ice cooling. The ice bath was removed, and the mixture was stirred at room temperature for 1 hour. The reaction mixture was concentrated under reduced pressure, and the resultant crude crystals were recrystallized from methanol-diethyl ether, thereby obtaining 412 mg (yield: 82%) of the title compound as colorless needles (melting point: 280° C. or higher).

Referential Example 7

Preparation of N,N'-bis(4-piperidinyl)-N,N'-dimethyl-ethylenediamine tetrahydrochloride

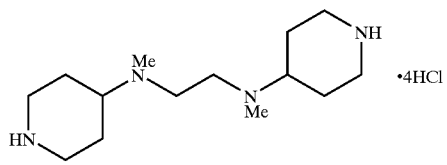

After 1-benzyl-4-piperidone (5.00 g; 26 mmol) and sodium cyanoborohydride (1.25 g; 20 mmol) were added to a solution of N,N'-dimethylethylenediamine (785 mg; 8.9 mmol) in methanol (20 ml) under ice cooling. The ice bath was removed, and acetic acid (2.5 ml; 44 mmol) was added to the solution, and the mixture was stirred for 15 minutes. Potassium carbonate (3 g; 22 mmol) and a saturated aqueous solution of sodium hydrogencarbonate was added to the reaction mixture to conduct extraction with chloroform. The organic layer was washed with saturated brine, dried over anhydrous sodium sulfate and then concentrated under reduced pressure. The resultant crude oil was purified by column chromatography on silica gel, thereby obtaining 955 mg (yield: 25%) of N,N'-bis(1-benzyl-4-piperidinyl)-N,N'-dimethylethylenediamine as a colorless oil.

10% Palladium on carbon (125 mg) and concentrated hydrochloric acid (1.2 ml; 14 mmol) were added to a solution in water-methanol (4 ml–8 ml) of N,N'-bis(1-benzyl-4-piperidinyl)-N,N'-dimethylethylenediamine (757 mg; 1.7 mmol) synthesized by the above process, and the mixture was stirred for 6 hours in a bath controlled at 55° C. under hydrogen. The catalyst was removed from the reaction mixture by filtration, and the filtrate was concentrated under reduced pressure. The resultant crude crystals were washed with ethanol, thereby obtaining 497 mg (yield: 71%) of the title compound as a colorless crystalline powder [melting point: 275° C. (decomposition)].

Referential Example 8

Preparation of 1,4-bis[(4-piperidinyl)methyl]-piperazine tetrahydrochloride

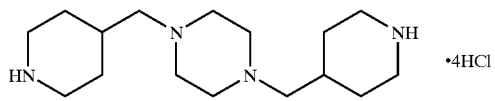

After a solution of methanesulfonyl chloride (0.17 ml; 2.2 mmol) in methylene chloride (1 ml) was added to a solution in methylene chloride (3 ml) of (1-tert-butoxy-carbonyl-4-piperazinyl)methyl alcohol (400 mg; 1.9 mmol) and N,N-diisopropylethylamine (0.45 ml; 2.6 mmol) under ice cooling, and the mixture was stirred for 2 hours. The ice bath was removed, and the mixture was stirred at room temperature for 5 hours. Water was added to the reaction mixture to conduct extraction with ethyl acetate. The organic layer was washed successively with 0.1N hydrochloric acid, an aqueous solution of sodium hydrogen-carbonate and saturated brine, dried over anhydrous sodium sulfate and then concentrated under reduced pressure, thereby obtaining crude crystals (645 mg) of (1-tert-butoxycarbonyl-4-piperazinyl) methyl methanesulfonate.

Piperazine (86 mg; 1.0 mmol), potassium carbonate (415 mg; 3.0 mmol) and potassium iodide (366 mg; 2.2 mmol)

were added to a solution in dimethylformamide (7 ml) of the crude crystals of (1-tert-butoxycarbonyl-4-piperazinyl)-methyl methanesulfonate (645 mg; about 2.2 mmol) synthesized by the above process, and the mixture was stirred for 2 hours in a bath controlled at 80° C. Water was added to the reaction mixture to conduct extraction with chloroform. The organic layer was washed with saturated brine, dried over anhydrous sodium sulfate and then concentrated under reduced pressure. The resultant crude oil was purified by column chromatography on silica gel, thereby obtaining 205 mg (yield: 41%) of 1,4-bis[(1-tert-butoxycarbonyl-4-piperidinyl)methyl]piperazine as a colorless oil.

A 4N hydrogen chloride in ethyl acetate (4 ml; 16 mmol) was added to a solution in methylene chloride (2 ml) of 1,4-bis[(1-tert-butoxycarbonyl-4-piperidinyl)methyl]-piperazine (195 mg; 0.40 mmol) synthesized by the above process under ice cooling, and the mixture was stirred for 30 minutes. The ice bath was removed, and the mixture was stirred at room temperature for 12 hours. The reaction mixture was concentrated under reduced pressure, and the resultant crude crystals were recrystallized from methylene chloride-methanol-diethyl ether, thereby obtaining 154 mg (yield: 84%) of the title compound as a colorless crystalline powder (melting point: 280° C. or higher).

Example 1

Preparation of 1,2-bis[4-[(E,E)-5-(3,4,5-trimethoxyphenyl)-2,4-pentadienoyl]-1-piperazinyl]ethane dihydrochloride After oxalyl chloride (0.055 ml; 0.63 mmol) was added to a solution of (E,E)-5-(3,4,5-trimethoxyphenyl)-2, 4-pentadienoic acid (116 mg; 0.44 mmol) in dimethylformamidemethylene chloride (0.1ml–5 ml) under ice cooling. The ice bath was removed, and the mixture was stirred at room temperature for 30 minutes. The reaction mixture was concentrated under reduced pressure to obtain crude crystals of (E,E)-5-(3,4,5-trimethoxyphenyl)-2,4-pentadienoyl chloride.

N,N-Diisopropylethylamine (0.12 ml; 0.69 mmol) was added to a solution in methylene chloride (3 ml) of 1,2-bis(1-piperazinyl)ethane tetrahydrochloride (69 mg; 0.20 mmol) synthesized by the same process as in Referential Example 1 under ice cooling. A solution in methylene chloride (3 ml) of (E,E)-5-(3,4,5-trimethoxyphenyl)-2,4-pentadienoyl chloride synthesized by the above process was further added dropwise to this solution under ice cooling. After completion of the addition, the mixture was stirred for 1 hour. A 5% aqueous solution of sodium hydrogencarbonate was added to the reaction mixture to conduct extraction with chloroform. The organic layer was dried over anhydrous sodium sulfate and then concentrated under reduced pressure. The resultant crude oil was purified by column chromatography on silica gel, thereby obtaining 133 mg (yield: 99%) of 1,2-bis[4-[(E,E)-5-(3,4,5-trimethoxyphenyl)-2,4-pentadienoyl]-1-piperazinyl]ethane as a colorless oil.

Concentrated hydrochloric acid (0.050 ml; 0.60 mmol) was added to a solution in ethanol (5 ml) of 1,2-bis[4-[(E,E)-5-(3,4,5-trimethoxyphenyl)-2,4-pentadienoyl]-1-piperazinyl]ethane (128 mg; 0.19 nmmol) synthesized in the above process and the reaction mixture was concentrated under reduced pressure. After a process of adding ethanol (10 ml) to the residue and concentrating the mixture under reduced pressure was performed twice, the resultant concentrated residue was recrystallized from methanoldiethyl ether to obtain the title compound as a pale yellow crystalline powder.

Melting point: 265–267° C.

$^1$H-NMR (data of free base of the title compound) (DMSO-$d_6$, 120° C.) δ: 2.80–2.90(m,12H), 3.54(dd,J=5.0,

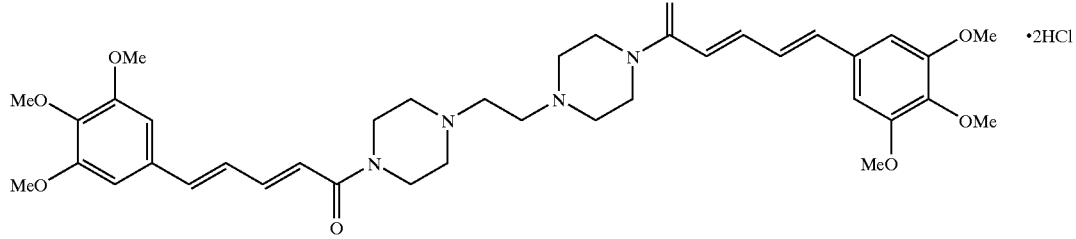

5.0 Hz,8H), 3.72(s,6H), 3.82(s,12H), 6.62(d,J=14.7 Hz,2H), 6.80(s,4H), 6.81(d,J=15.4 Hz,2H), 6.96(dd,J=15.4,10.7 Hz,2H), 7.19(dd,J=14.7,10.3 Hz,2H).

Example 2

Preparation of 1,2-bis[4-[4-(3,4,5-trimethoxyphenyl)benzoyl]-1-piperazinyl]ethane dihydrochloride

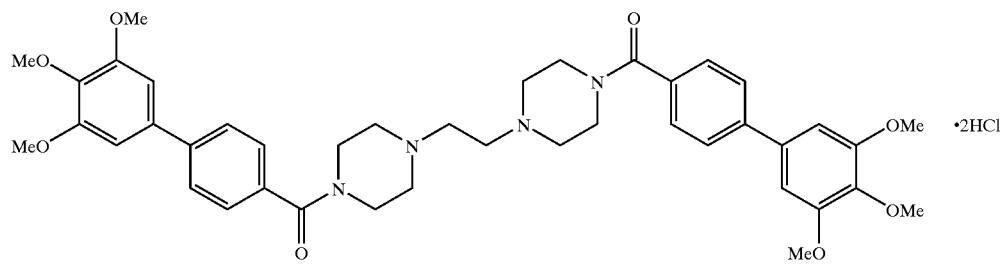

In accordance with the same process as in Example 1, 1,2-bis[4-[4-(3,4,5-trimethoxyphenyl)benzoyl]-1-piperazinyl]ethane (84 mg; yield: 71%) was obtained as a colorless oil from 4-(3,4,5-trimethoxyphenyl)benzoic acid (97 mg; 0.34 mmol) and 1,2-bis(1-piperazinyl)ethane tetrahydrochloride (55 mg; 0.16 mmol) synthesized by the same process as in Referential Example 1.

Concentrated hydrochloric acid (0.028 ml; 0.34 mmol) was added to a solution of 1,2-bis[4-[4-(3,4,5-trimethoxyphenyl)benzoyl]-1-piperazinyl]ethane (84 mg; 0.11 mmol) in ethanol (5 ml) and the reaction mixture was concentrated under reduced pressure. A process of adding ethanol (10 ml) to the residue and concentrating the mixture under reduced pressure was performed twice. The resultant crude crystals were suspended in methanol and collected by filtration to obtain the title compound as a colorless crystalline powder.

Melting point: 282–285° C.

$^1$H-NMR (data of free base of the title compound) (DMSO-d$_6$, 120° C.) δ: 2.40–2.70(m,12H), 3.40–3.60(m, 4H), 3.70–3.90(m,4H), 3.74(s,6H), 3.90(s,12H), 6.77(s,4H), 7.47(d,J=8.3 Hz,4H), 7.59(d,J=8.3 Hz,4H).

Example 3

Preparation of 1,3-bis[4-[(E,E)-5-(3,4,5-trimethoxyphenyl)-2,4-pentadienoyl]-1-piperazinyl] propane dihydrochloride

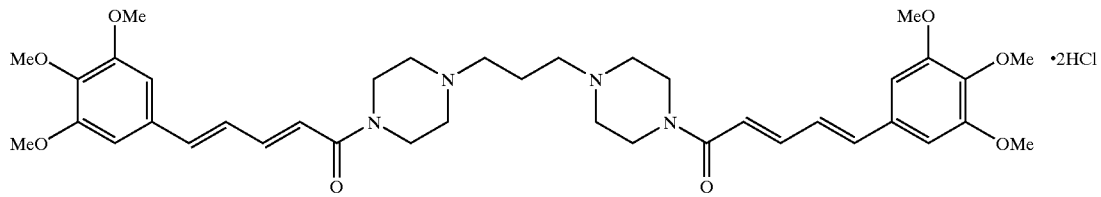

In accordance with the same process as in Example 1, 1,3-bis[4-[(E,E)-5-(3,4,5-trimethoxyphenyl)-2,4-pentadienoyl]-1-piperazinyl]propane (135 mg; yield: 86%) was obtained as a pale yellow oil from (E,E)-5-(3,4,5-trimethoxyphenyl)pentadienoic acid (130 mg; 0.49 mmol) and 1,3-bis(1-piperazinyl)propane tetrahydrochloride (80 mg; 0.22 mmol) synthesized by the process described in Referential Example 1.

Concentrated hydrochloric acid (0.040 ml; 0.48 mmol) was added to a solution of 1,3-bis[4-[(E,E)-5-(3,4,5-trimethoxyphenyl)-2,4-pentadienoyl]-1-piperazinyl] propane (130 mg; 0.19 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as a pale yellow crystalline powder.

Melting point: 263–265° C.

$^1$H-NMR (DMSO-d$_6$, 120° C.) (no NH$^+$ proton of the ammonium salt was observed) δ: 2.15–2.30(m,2H), 2.80–3.30(m,16H), 3.73(s,6H), 3.82(s,12H), 3.85–4.00(m, 4H), 6.65(d,J=14.7 Hz,2H), 6.81(s,4H), 6.87(d,J=15.4 Hz,2H), 6.97(dd,J=15.4,9.7 Hz,2H), 7.27(dd,J=14.7,9.7 Hz,2H).

Example 4

Preparation of 1,3-bis[4-[(E,E)-5-(4-tert-butyl-2-methoxyphenyl)-2,4-pentadienoyl]-1-piperazinyl] propane dihydrochloride

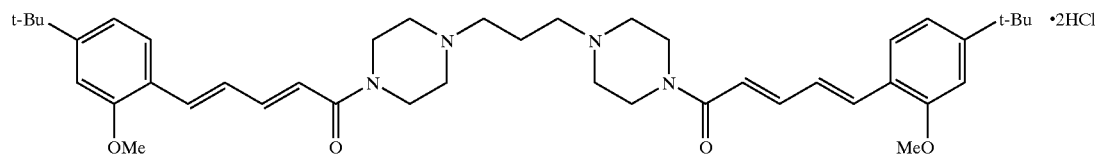

In accordance with the same process as in Example 1, 1,3-bis[4-[(E,E)-5-(4-tert-butyl-2-methoxyphenyl)-2,4-pentadienoyl]-1-piperazinyl]propane (52 mg; yield: 75%) was obtained as a pale yellow oil from (E,E)-5-(4-tert-butyl-2-methoxyphenyl)-2,4-pentadienoic acid (57 mg; 0.22 mmol) and 1,3-bis(1-piperazinyl)propane tetrahydrochloride (35 mg; 0.10 mmol) synthesized by the process described in Referential Example 1.

Concentrated hydrochloric acid (0.025 ml; 0.30 mmol) was added to a solution of 1,3-bis[4-[(E,E)-5-(4-tert-butyl-2-methoxyphenyl)-2,4-pentadienoyl]-1-piperazinyl]-propane (49 mg; 0.070 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (data of free base of the title compound) (DMSO-d$_6$, 120° C.) δ: 1.30(s,18H), 1.58–1.67(m,2H), 2.33–2.43(m,12H), 3.49–3.59(m,8H), 3.85(s,6H), 6.57(d,J= 14.6 Hz,2H), 6.90–7.01(m,6H), 7.04(d,J=15.6 Hz,2H), 7.20 (dd,J=14.6,10.0 Hz,2H), 7.40(d,J=8.0 Hz,2H).

Example 5

Preparation of 1,3-bis[4-[4-(3,4,5-trimethoxyphenyl) benzoyl]-1-piperazinyl]propane dihydrochloride

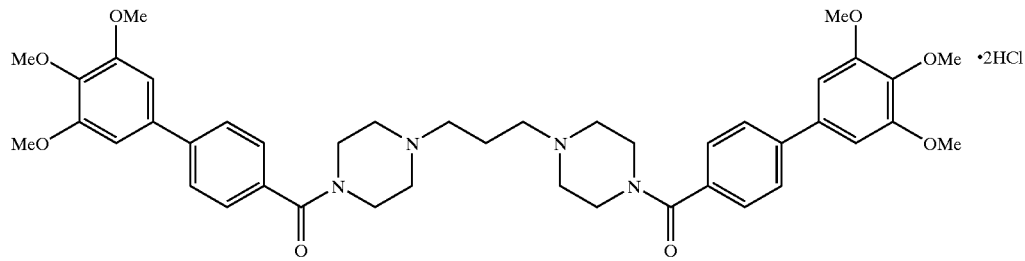

In accordance with the same process as in Example 1, 1,3-bis[4-[4-(3,4,5-trimethoxyphenyl)benzoyl]-1-piperazinyl]propane (43 mg; yield: 57%) was obtained as a colorless oil from 4-(3,4,5-trimethoxyphenyl)benzoic acid (64 mg; 0.21 mmol) and 1,3-bis(1-piperazinyl)propane tetrahydrochloride (35 mg; 0.10 mmol) synthesized by the process described in Referential Example 1.

Concentrated hydrochloric acid (0.015 ml; 0.18 mmol) was added to a solution of 1,3-bis[4-[4-(3,4,5-trimethoxyphenyl)benzoyl]-1-piperazinyl]propane (43 mg; 0.050 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as a colorless crystalline powder.

Melting point: 262–265° C.

$^1$H-NMR (DMSO-$d_6$, 120° C.) (no NH$^+$ proton of the ammonium salt was observed) δ: 2.05–2.20(m,2H), 2.60–3.40(m,12H), 3.75(s,6H), 3.72–3.84(m,8H), 3.87(s, 12H), 6.92(s,4H), 7.49(d,J=8.0 Hz,2H), 7.71(d,J=8.0 Hz,2H).

Example 6

Preparation of 1,3-bis[4-[(E)-5-(3,4,5-trimethoxyphenyl)-2-penten-4-ynoyl]-1-piperazinyl] propane dihydrochloride In accordance with the same process as in Example 1, 1,3-bis[4-[(E)-5-(3,4,5-trimethoxyphenyl)-2-penten-4-ynoyl]-1-piperazinyl]propane (114 mg; yield: 81%) was obtained as a pale yellow oil from (E)-5-(3,4,5-trimethoxphenyl)-2-penten-4-ynoic acid (110 mg; 0.42 mmol) and 1,3-bis(1-piperazinyl)propane tetrahydrochloride (72 mg; 0.2 mmol) synthesized by the process described in Referential Example 1.

Concentrated hydrochloric acid (0.060 ml; 0.72 mmol) was added to a solution of 1,3-bis[4-[(E)-5-(3,4,5-trimethoxyphenyl)-2-penten-4-ynoyl]-1-piperazinyl] propane (114 mg; 0.15 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from ethanol-diethyl ether to obtain the title compound as a pale yellow crystalline powder.

Melting point: 235–237° C.

$^1$H-NMR (DMSO-$d_6$, 120° C.) (no NH$^+$ proton of the ammonium salt was observed) δ: 2.11–2.23(m,2H), 2.70–3.25(m,12H), 3.74(s,6H), 3.80(s,12H), 3.82–4.01(m, 8H), 6.77(s,4H), 6.80(d,J=15.3 Hz,2H), 7.01(d,J=15.3 Hz,2H).

Example 7

Preparation of 1,3-bis[4-[3-(3,4,5-trimethoxyphenyl)-2-propynoyl]-1-piperazinyl]propane

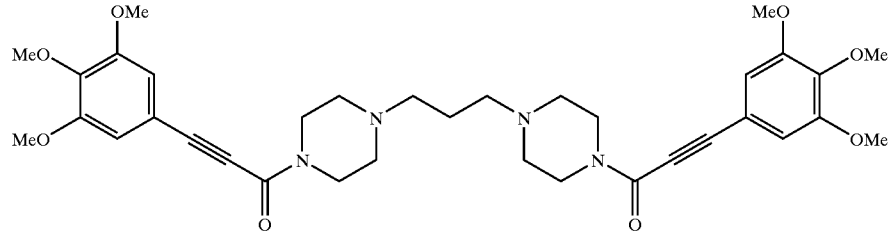

1,3-Bis(1-piperazinyl)propane tetrahydrochloride (57 mg; 0.16 mmol) synthesized by the process described in Referential Example 1 and N,N-diisopropylethylamine (0.28 ml; 1.6 mmol) were added to a solution of 3-(3,4,5-trimethoxyphenyl)-2-propynoic acid (80 mg; 0.34 mmol) in tetrahydrofuran (3 ml). Diethyl phosphorocyanidate (0.055 ml; 0.37 mmol) was gradually added to the mixture under ice cooling. An ice bath was removed, and the mixture was stirred at room temperature for 1 hour and water was added to the reaction mixture to conduct extraction with chloroform. The organic layer was washed with saturated brine, dried over anhydrous sodium sulfate and then concentrated under reduced pressure. The resultant crude oil was purified by column chromatography on silica gel to obtain crude crystals. The crude crystals thus obtained were recrystallized from chloroform-acetone-diethyl ether to obtain 75 mg (yield: 72%) of the title compound as colorless needles.

Melting point: 214–215° C.

$^1$H-NMR (DMSO-$d_6$, 120° C.) δ: 1.66(tt,J=7.1,7.1 Hz,2H), 2.40–2.53(m,4H), 3.50–3.88(m,16H), 3.77(s,6H), 3.82(s,12H), 6.84(s,4H).

Example 8

Preparation of 1,3-bis[4-[5-nitro-2-(3,4,5-trimethoxyphenyl)benzoyl]-1-piperazinyl]propane dihydrochloride

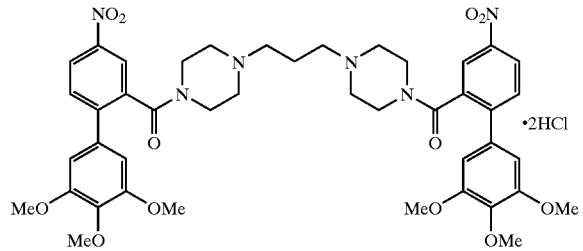

In accordance with the same process as in Example 7, 1,3-bis[4-[5-nitro-2-(3,4,5-trimethoxyphenyl)benzoyl]-1-piperazinyl]propane (234 mg; yield: 69%) was obtained as a pale yellow oil from 5-nitro-2-(3,4,5-trimethoxyphenyl)benzoic acid (280 mg; 0.84 mmol) and 1,3-bis(1-piperazinyl)propane tetrahydrochloride (143 mg; 0.40 mmol) synthesized by the process described in Referential Example 1.

Concentrated hydrochloric acid (0.090 ml; 1.1 mmol) was added to a solution of 1,3-bis[4-[5-nitro-2-(3,4,5-trimethoxyphenyl)benzoyl]-1-piperazinyl]propane (230 mg; 0.27 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.80–1.95(m,2H), 2.70–2.80(m,4H), 2.60–3.50(m,16H), 3.74(s,6H), 3.81(s,12H), 6.75(s,4H), 7.77(d,J=8.5 Hz,2H), 8.19(d,J=2.4 Hz,2H), 8.28(dd,J=8.5,2.4 Hz,2H).

Example 9

Preparation of 1,3-bis[4-[5-amino-2-(3,4,5-trimethoxyphenyl)benzoyl]-1-piperazinyl]propane dihydrochloride

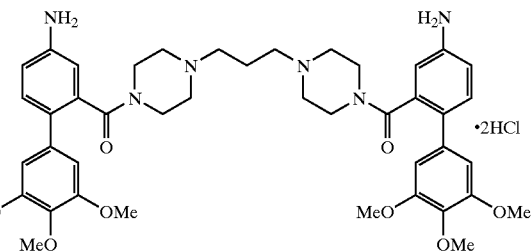

10% Palladium on carbon (50 mg) was added to a solution in acetic acid-methanol (1 ml-i ml) of 1,3-bis[4-[5-nitro-2-(3,4,5-trimethoxyphenyl)benzoyl]-1-piperazinyl]-propane dthydrochloride (91 mg; 0.10 mmol) synthesized by the process described in Example 8. After the mixture was stirred at room temperature for 3 hours under hydrogen, the catalyst was removed from the reaction mixture by filtration. The filtrate was concentrated under reduced pressure, and a saturated aqueous solution of sodium hydrogencarbonate was added to the resultant concentrated residue to conduct extraction with chloroform. The organic layer was washed with saturated brine, dried over anhydrous sodium sulfate and then concentrated under reduced pressure. The resultant crude oil was purified by column chromatography on silica gel, thereby obtaining 29 mg (yield: 37%) of 1,3-bis[4-[5-amino-2-(3,4,5-trimethoxyphenyl)benzoyl]-1-piperazinyl]propane as a colorless oil.

Concentrated hydrochloric acid (0.020 ml; 0.24 mmol) was added to a solution of 1,3-bis[4-[5-amino-2-(3,4,5-trimethoxyphenyl)benzoyl]-1-piperazinyl]propane (29 mg; 0.030 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methylene chloride-diethyl ether to obtain the title compound as a pale yellow crystalline powder.

Hz,2H), 7.03(d,J=15.6 Hz,2H), 7.15(dd,J=15.6,10.4 Hz,2H), 7.30(dd,J=14.6,10.4 Hz,2H), 7.65–7.73(m,8H).

Example 11

Preparation of 1,4-bis[4-[4-(3,4,5-trimethoxyphenyl)benzoyl]-1-piperazinyl]butane dimethanesulfonate

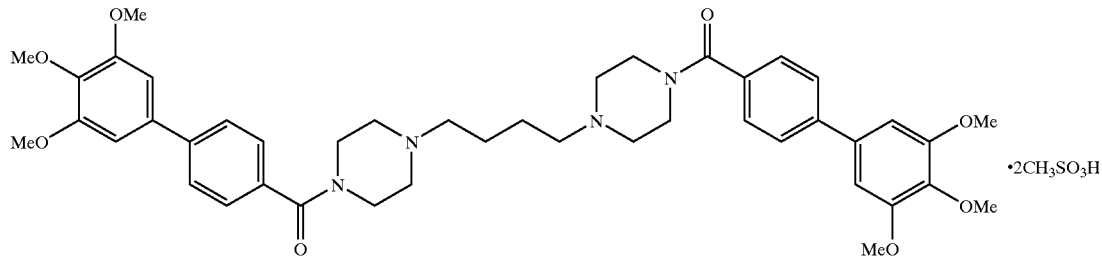

Melting point: 230° C. (decomposition).
$^1$H-NMR (DMSO-d$_6$, 120° C.) (no NH$^+$ proton of the ammonium salt was observed) δ: 1.90–2.15(m,2H), 2.60–3.01(m,4H), 3.20–4.50(m,16H), 3.73(s,6H), 3.78(s, 12H), 6.60(s,4H), 6.72(br s,2H), 6.86(br d,J=8.2 Hz,2H), 7.23(br d,J=8.2 Hz,2H).

Example 10

Preparation of 1,3-bis[4-[(E,E)-5-(4-trifluoromethylphenyl)-2,4-pentadienoyl]-1-piperazinyl]propane dihydrochloride In accordance with the same process as in Example 7, 1,4-bis[4-[4-(3,4,5-trimethoxyphenyl)benzoyl]-1-piperazinyl]butane (110 mg; yield: 84%) was obtained as a colorless oil from 4-(3,4,5-trimethoxyphenyl)benzoic acid (103 mg; 0.36 mmol) and 1,4-bis(1-piperazinyl)butane tetrahydrochloride (63 mg; 0.17 mmol) synthesized by the same process as in Referential Example 1.

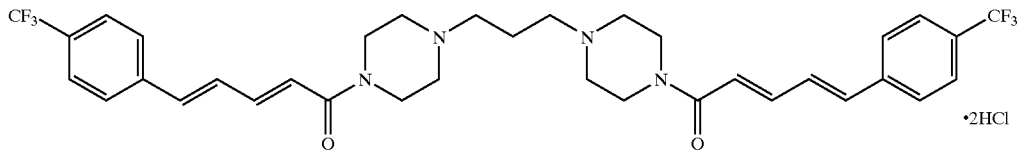

In accordance with the same process as in Example 7, 1,3-bis[4-[(E,E)-5-(4-trifluoromethylphenyl)-2,4-pentadienoyl]-1-piperazinyl]propane (111 mg; yield: 84%) was obtained as a colorless amorphous powder from (E,E)-5-(4-trifluoromethylphenyl)-2,4-pentadienoic acid (107 mg; 0.44 mmol) and 1,3-bis(1-piperazinyl)propane tetrahydrochloride (72 mg; 0.20 mmol) synthesized by the process described in Referential Example 1.

Concentrated hydrochloric acid (0.040 ml; 0.48 mmol) was added to a solution of 1,3-bis[4-[(E,E)-5-(4-trifluoromethylphenyl)-2,4-pentadienoyl]-1-piperazinyl]propane (111 mg; 0.16 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from ethanol-diethyl ether to obtain the title compound as a colorless crystalline powder.

Melting point: 241° C. (decomposition).

$^1$H-NMR (DMSO-d$_6$, 120° C.) (no NH$^+$ proton of the ammonium salt was observed) δ: 2.20(t,J=7.3 Hz,2H), 2.55–3.65(m,12H), 3.75–4.20(m,8H), 6.76(d,J=14.6

A 0.1 M aqueous solution of methanesulfonic acid (3.0 ml; 0.30 mmol) was added to a solution of 1,4-bis[4-[4-(3, 4,5-trimethoxyphenyl)benzoyl]-1-piperazinyl]butane (110 mg; 0.14 mmol) in ethanol (15 ml) and the reaction mixture was concentrated under reduced pressure. After a process of adding ethanol (15 ml) to the residue and concentrating the mixture under reduced pressure was performed 3 times, the resultant concentrated residue was recrystallized from methanol-diethyl ether to obtain the title compound as colorless prisms.

Melting point: 166–169° C. (decomposition).

$^1$H-NMR (DMSO-d$_6$, 120° C.) (no NH$^+$ proton of the ammonium salt was observed) δ: 1.70–1.80(m,4H), 2.38(s, 6H), 2.90–3.20(m,16H), 3.76(s,6H), 3.87(s,12H), 3.70–3.90 (m,4H), 6.92(s,4H), 7.50(d,J=8.3 Hz,4H), 7.72(d,J=8.3 Hz,4H).

Example 12

Preparation of 1,8-bis[4-[(E,E)-5-(4-tert-butylphenyl)-2,4-pentadienoyl]-1-piperazinyl]octane dihydrochloride

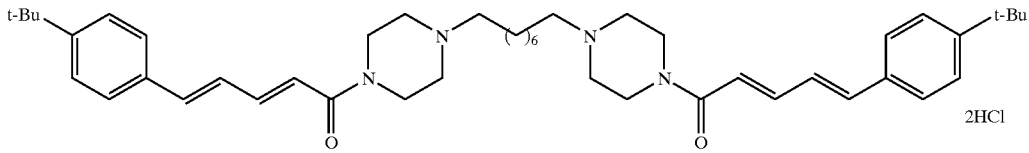

In accordance with the same process as in Example 7, 1,8-bis[4-[(E,E)-5-(4-tert-butylphenyl)-2,4-pentadienoyl]-1-piperazinyl]octane (105 mg; yield: 72%) was obtained as a colorless oil from (E,E)-5-(4-tert-butylphenyl)-2,4-pentadienoic acid (101 mg; 0.40 mmol) and 1,8-bis(1-piperazinyl)octane tetrahydrochloride (86 mg; 0.20 mmol) synthesized by a process similar to the process described in Referential Example 1.

Concentrated hydrochloric acid (0.050 ml; 0.60 mmol) was added to a solution of 1,8-bis[4-[(E,E)-5-(4-tert-butylphenyl)-2,4-pentadienoyl]-1-piperazinyl]octane (105 mg; 0.14 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as a colorless crystalline powder.

Melting point: 288–290° C.

$^1$H-NMR (DMSO-$d_6$, 120° C.) (no NH$^+$ proton of the ammonium salt was observed) δ: 1.27(s,18H), 1.28–1.32(m, 8H), 1.43–1.46(m,4H), 2.30–2.34(m,4H), 2.38(dd,J=5.1,5.1 Hz,8H), 3.54(dd,J=5.1,5.1 Hz,8H), 6.60(d,J=14.6 Hz,2H), 6.86(d,J=15.6 Hz,2H), 6.95(dd,J=15.6,10.2 Hz,2H), 7.21 (dd,J=14.6,10.2 Hz,2H), 7.36(d,J=8.5 Hz,4H), 7.41(d,J=8.5 Hz,4H).

Example 13

Preparation of 1,8-bis[4-[(E,E)-5-(2-methylthio-3-pyridyl)-2,4-pentadienoyl]-1-piperazinyl]octane dihydrochloride

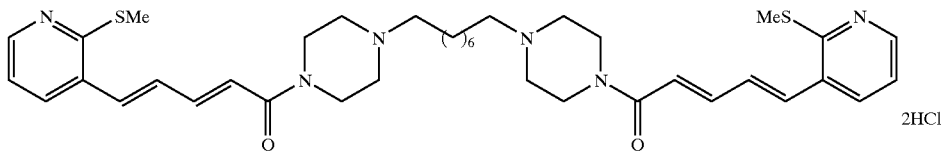

In accordance with the same process as in Example 7, a pale yellow oil containing 1,8-bis[4-[(E,E)-5-(2methylthio-3-pyridyl)-2,4-pentadienoyl]-1-piperazinyl]-octane was obtained from (E,E)-5-(2-methylthio-3-pyridyl)2,4-pentadienoic acid (114 mg; 0.44 mmol) and 1,8-bis(1-piperazinyl)octane tetrahydrochloride (86 mg; 0.20 mmol) synthesized by a process similar to the process described in Referential Example 1.

Concentrated hydrochloric acid (0.085 ml; 1.0 mmol) was added to a solution of this pale yellow oil in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from ethanol-diethyl ether to obtain 71 mg (yield: 47%) of the title compound as a pale yellow crystalline powder.

Melting point: 190° C. (decomposition).

$^1$H-NMR (data of free base of the title compound) (CDCl$_3$) δ: 1.20–1.40(m,8H), 1.40–1.60(m,4H), 2.30–2.40 (m,4H), 2.40–2.50(m,8H), 2.59(s,6H), 3.50–3.80(m,8H), 6.48(d,J=14.9 Hz,2H), 6.83(dd,J=15.3,10.0 Hz,2H), 7.00 (dd,J=7.6,4.8 Hz,2H), 7.08(d,J=15.3 Hz,2H), 7.47(dd,J= 14.9,10.0 Hz,2H), 7.64(dd,J=7.6,1.7 Hz,2H), 8.37(dd,J=4.8, 1.7 Hz,2H).

Example 14

Preparation of 1,4-bis[[4-[4-(3,4,5-trimethoxyphenyl)benzoyl]-1-piperazinyl]methyl]cyclohexane dihydrochloride

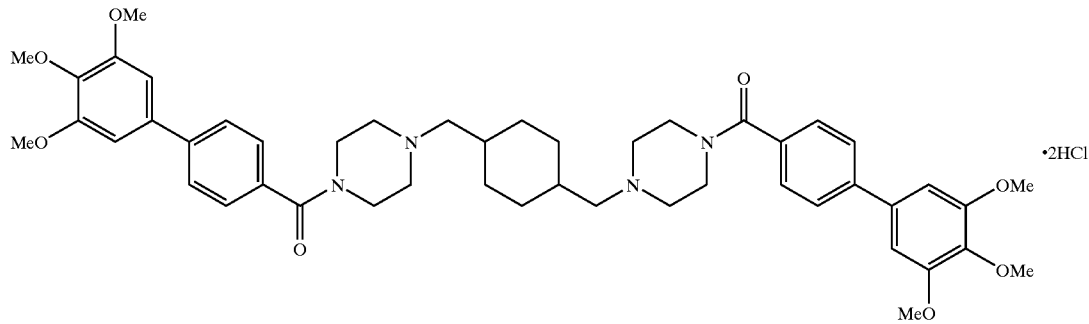

In accordance with the same process as in Example 7, crude crystals (118 mg) of 1,4-bis[[4-[4-(3,4,5-trimethoxyphenyl)benzoyl]-1-piperazinyl]methyl]cyclohexane were obtained from 4-(3,4,5-trimethoxyphenyl)benzoic acid (122 mg; 0.44 mmol) and 1,4-bis[(1-piperazinyl)methyl]-cyclohexane tetrahydrochloride (85 mg; 0.20 mmol) synthesized by a process similar to the process described in Referential Example 1.

Concentrated hydrochloric acid (0.050 ml; 0.60 mmol) was added to a solution of the crude crystals of 1,4-bis[[4-[4-(3,4,5-trimethoxyphenyl)benzoyl]-1-piperazinyl]methyl]cyclohexane (118 mg; 0.14 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from chloroform-methanol-diethyl ether to obtain 105 mg (yield: 58%) of the title compound as a pale yellow crystalline powder.

Melting point: 280° C. or higher.

$^1$H-NMR (data of free base of the title compound) (CDCl$_3$) δ: 0.80–0.90(m,4H), 1.85–2.05(m,2H), 1.80–1.90 (m,4H), 2.16(d,J=7.0 Hz,4H), 2.25–2.60(m,8H), 3.40–3.80 (m,8H), 3.89(s,6H), 3.93(s,12H), 6.77(s,4H), 7.47(d,J=8.2 Hz,4H), 7.58(d,J=8.2 Hz,4H).

Example 15

Preparation of 1,4-bis[[4-[(E,E)-5-(4-chlorophenyl)-2,4-pentadienoyl]-1-piperazinyl]methyl]cyclohexane dihydrochloride

In accordance with the same process as in Example 7, crude crystals (72 mg) of 1,4-bis[[4-[(E,E)-5-(4-chlorophenyl)-2,4-pentadienoyl]-1-piperazinyl]methyl]cyclohexane were obtained from (E,E)-5-(4-chlorophenyl)-2,4-pentadienoic acid (92 mg; 0.44 mmol) and 1,4-bis[(1-piperazinyl)methyl]cyclohexane tetrahydrochloride (85 mg; 0.20 mmol) synthesized by a process similar to the process described in Referential Example 1.

Concentrated hydrochloric acid (0.030 ml; 0.36 mmol) was added to a solution in ethanol (5 ml) of the crude crystals (72 mg; 0.090 mmol) of 1,4-bis[[4-[(E,E)-5-(4-chlorophenyl)-2,4-pentadienoyl]-1-piperazinyl]-cyclohexane and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain 66 mg (yield: 50%) of the title compound as a colorless crystalline powder.

Melting point: 284° C. (decomposition).

$^1$H-NMR (data of free base of the title compound) (CDCl$_3$) δ: 0.80–1.0(m,4H), 1.40–1.50(m,2H), 1.75–1.95 (m,4H), 2.15(d,J=7.3 Hz,4H), 2.30–2.51(m,8H), 3.50–3.80 (m,8H), 6.46(d,J=14.6 Hz,2H), 6.79(d,J=15.6 Hz,2H), 6.87 (d,J=15.6,10.0 Hz,2H), 7.29–7.39(m,8H), 7.42(dd,J=14.6, 10.0 Hz,2H).

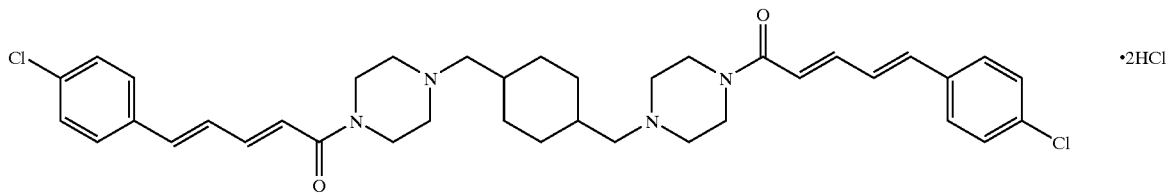

Example 16

Preparation of 1,4-bis[[4-[4-(3,4,5-trimethoxyphenyl)benzoyl]-1-piperazinyl]methyl]benzene dihydrochloride

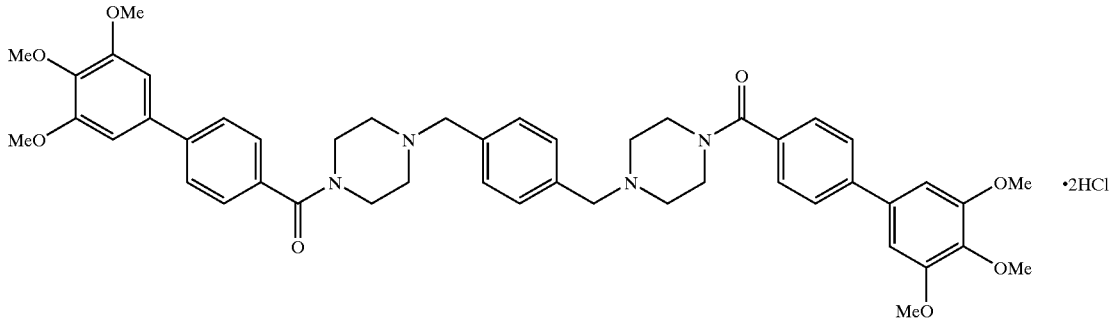

In accordance with the same process as in Example 7, 1,4-bis[[4-[4-(3,4,5-trimethoxyphenyl)benzoyl]-1-piperazinyl]methyl]benzene (157 mg; yield: 96%) was obtained as a colorless oil from 4-(3,4,5-trimethoxyphenyl) benzoic acid (122 mg; 0.44 mmol) and 1,4-bis[(1-piperazinyl)methyl]benzene tetrahydrochloride (84 mg; 0.20 mmol) synthesized by a process similar to the process described in Referential Example 1.

Concentrated hydrochloric acid (0.065 ml; 0.78 mmol) was added to a solution of 1,4-bis[[4-[4-(3,4,5-trimethoxyphenyl)benzoyl]-1-piperazinyl]methyl]benzene (157 mg; 0.19 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from chloroform-methanol-diethyl ether to obtain the title compound as a colorless crystalline powder.

Melting point: 264° C. (decomposition).

$^1$H-NMR (DMSO-$d_6$, 120° C.) (no NH$^+$ proton of the ammonium salt was observed) δ: 2.65–3.10(m,8H), 3.75(s, 6H), 3.82–3.86(m,8H), 3.86(s,12H), 4.15–4.30(m,4H), 6.91 (s,4H), 7.46(d,J=8.2 Hz,4H), 7.63(s,4H), 7.69(d,J=8.2 Hz,4H).

Example 17

Preparation of 1,4-bis[[4-[(E)-5-(3,4,5-trimethoxyphenyl)-2-penten-4-ynoyl]-1-piperazinyl]methyl]benzene dihydrochloride In accordance with the same process as in Example 7, 1,4-bis[[4-[(E)-5-(3,4,5-trimethoxyphenyl)-2-penten-4-ynoyl]-1-piperazinyl]methyl]benzene (127 mg; yield: 83%) was obtained as a pale yellow oil from (E)-5-(3,4,5-trimethoxyphenyl)-2-penten-4-ynoic acid (115 mg; 0.44 mmol) and 1,4-bis[(1-piperazinyl)methyl]benzene tetrahydrochloride (84 mg; 0.20 mmol) synthesized by a process similar to the process described in Referential Example 1.

Concentrated hydrochloric acid (0.055 ml; 0.66 mmol) was added to a solution of 1,4-bis[[4-[(E)-5-(3,4,5-trimethoxyphenyl)-2-penten-4-ynoyl]-1-piperazinyl] methyl]benzene (127 mg; 0.16 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methylene chloride-methanol-diethyl ether to obtain the title compound as a pale yellow crystalline powder.

Melting point: 268° C. (decomposition).

$^1$H-NMR (DMSO-$d_6$, 120° C.) (no NH$^+$ proton of the ammonium salt was observed) δ: 1.70–3.40(m,12H), 3.65–3.90(m,4H), 3.74(s,6H), 3.79(s,12H), 4.00–4.25(m, 4H), 6.77(s,4H), 6.78(d,J=15.3 Hz,2H), 6.98(d,J=15.3 Hz,2H), 7.58(s,4H).

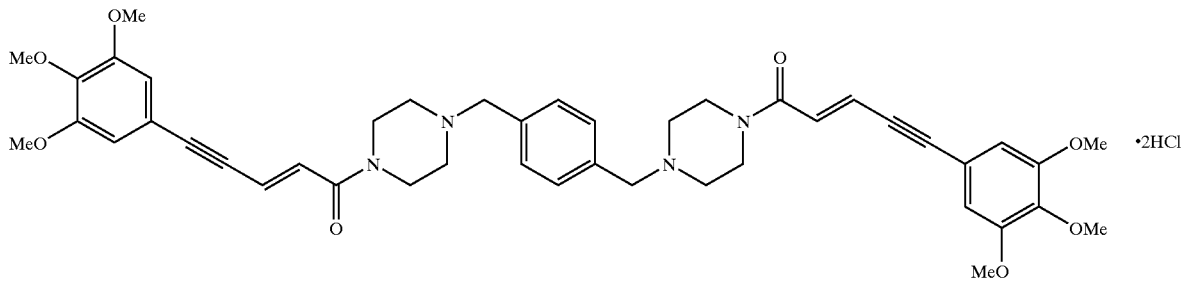

Example 18

Preparation of 1,4-bis[[4-[(E,E)-5-(3,4,5-trimethylphenyl)-2,4-pentadienoyl]-1-piperazinyl]methyl]benzene dihydrochloride

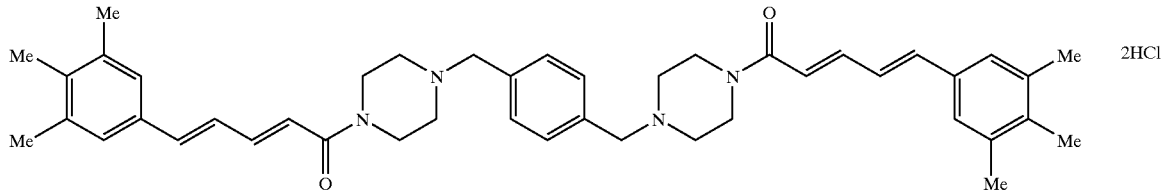

In accordance with the same process as in Example 7, 1,4-bis[[4-[(E,E)-5-(3,4,5-trimethylphenyl)-2,4-pentadienoyl]-1-piperazinyl]methyl]benzene (100 mg) was obtained as a colorless crystalline powder from (E,E)-5-(3,4,5-trimethylphenyl)-2,4-pentadienoic acid (95 mg; 0.44 mmol) and 1,4-bis[(1-piperazinyl)methyl]benzene tetrahydrochloride (84 mg; 0.20 mmol) synthesized by a process similar to the process described in Referential Example 1.

Concentrated hydrochloric acid (0.050 ml; 0.60 mmol) was added to a solution of 1,4-bis[[4-[(E,E)-5-(3,4,5-trimethylphenyl)-2,4-pentadienoyl]-1-piperazinyl]-methyl]benzene (100 mg; 0.14 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain 69 mg (yield: 47%) of the title compound as a colorless crystalline powder.

Melting point: 278° C. (decomposition).

$^1$H-NMR (data of free base of the title compound) (DMSO-$d_6$, 120° C.) δ: 2.13(s,6H), 2.24(s,12H), 2.38–2.44 (m,8H), 3.51(s,4H), 3.52–3.60(m,8H), 6.58(d,J=14.6 Hz,2H), 6.78(d,J=15.6 Hz,2H), 6.91(dd,J=15.6,10.7 Hz,2H), 7.10(s,4H), 7.19(dd,J=14.6,10.7 Hz,2H), 7.26(s,4H).

Example 19

Preparation of 2,6-bis[[4-[4-(3,4,5-trimethoxyphenyl)benzoyl]-1-piperazinyl]methyl]pyridine dihydrochloride In accordance with the same process as in Example 7, 2,6-bis[[4-[4-(3,4,5-trimethoxyphenyl)benzoyl]-1-piperazinyl]methyl]pyridine (157 mg; yield: 96%) was obtained as a colorless oil from 4-(3,4,5-trimethoxyphenyl) benzoic acid (126 mg; 0.44 mmol) and 2,6-bis[(1-piperazinyl)methyl]pyridine tetrahydrochloride (84 mg; 0.20 mmol) synthesized by a process similar to the process described in Referential Example 1.

Concentrated hydrochloric acid (0.080 ml; 0.96 mmol) was added to a solution of 2,6-bis[[4-[4-(3,4,5-trimethoxyphenyl)benzoyl]-1-piperazinyl]methyl]pyridine (157 mg; 0.19 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as a colorless crystalline powder.

Melting point: 224–226° C.

$^1$H-NMR (DMSO-$d_6$, 120° C.) (no NH$^+$ proton of the ammonium salt was observed) δ: 1.70–3.60(m,8H), 3.75(s, 6H), 3.86(s,12H), 3.86–4.01(m,8H), 4.35–4.50(m,4H), 6.91 (s,4H), 7.48(d,J=8.2 Hz,4H), 7.54(d,J=7.8 Hz,2H), 7.70(d, J=8.2 Hz,4H), 7.92(t,J=7.8 Hz,1H).

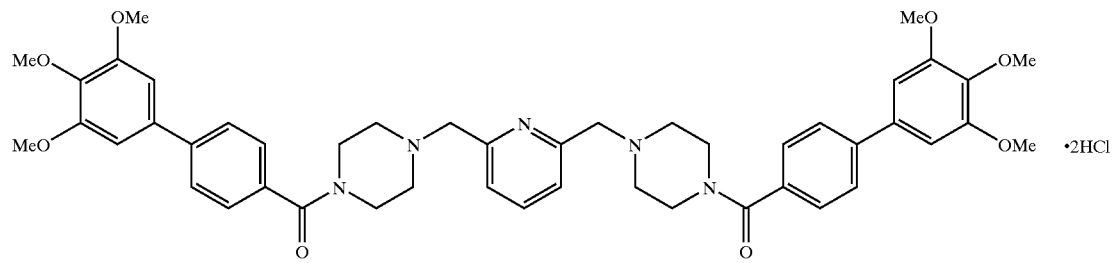

60

Example 20

Preparation of 2,6-bis[[4-[(E)-3-(2-naphthyl)-2-propenoyl]-1-piperazinyl]methyl]pyridine

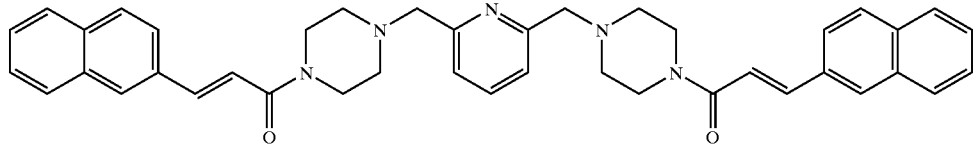

In accordance with the same process as in Example 7, crude crystals were obtained from (E)-3-(2-naphthyl)-2-propenoic acid (87 mg; 0.44 mmol) and 2,6-bis[(1-piperazinyl)methyl]pyridine tetrahydrochloride (92 mg; 0.22 mmol) synthesized by a process similar to the process described in Referential Example 1. The crude crystals thus obtained were recrystallized from chloroform-n-hexane to obtain 121 mg (yield: 95%) of the title compound as a colorless crystalline powder.

Melting point: 200–202° C.

$^1$H-NMR (DMSO-$d_6$, 120° C.) δ: 2.50–2.55(m,8H), 3.56–3.66(m,12H), 7.20(d,J=15.6 Hz,2H), 7.33(d,J=7.6 Hz,2H), 7.46–7.52(m,4H), 7.60(d,J=15.6 Hz,2H), 7.72(t,J=7.6 Hz,1H), 7.75–7.90(m,8H), 8.06(s,2H).

Example 21

Preparation of 1,4-bis[4-[4-(3,4,5-trimethoxyphenyl)benzoyl]-1-piperazinyl]benzene In accordance with the same process as in Example 1, crude crystals (35 mg; yield: 72%) were obtained from 4-(3,4,5-trimethoxyphenyl)benzoic acid (70 mg; 0.24 mmol) and 1,4-bis(1-piperazinyl)benzene (15 mg; 0.061 mmol) synthesized by the process described in Referential Example 2. The crude crystals thus obtained were recrystallized from chloroform-diethyl ether to obtain the title compound as a colorless crystalline powder.

Melting point: 218–219° C.

$^1$H-NMR (CDCl$_3$) δ: 2.90–3.30(m,8H), 3.50–3.70(m, 8H), 3.90(s,6H), 3.94(s,12H), 6.78(s,4H), 6.92(s,4H), 7.50 (d,J=8.3 Hz,4H), 7.61(d,J=8.3 Hz,4H).

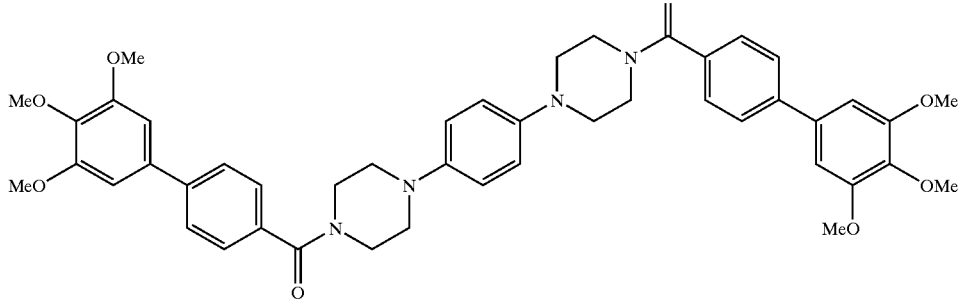

Example 22

Preparation of 1,1'-ethylenedi[4-[(E,E)-5-(3,5-dimethoxy-4-isopropoxyphenyl)-2,4-pentadienoyl]hexahydro-1,4-diazepine]

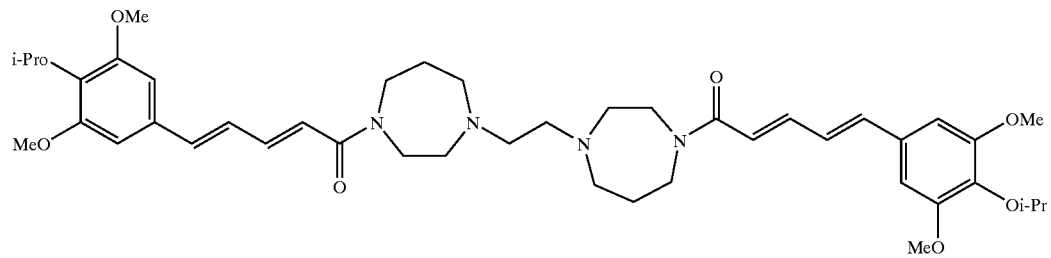

Potassium carbonate (0.50 g; 3.6 mmol) was added to a solution in water (1 ml) of 1,1'-ethylenedi(hexahydro-1,4-diazepine)tetrahydrochloride (385 mg; 1.0 mmol) synthesized in accordance with the same process as in Referential Example 1. The mixture was stirred at room temperature for 15 minutes and concentrated under reduced pressure. A process of adding ethanol (10 ml) to the residue and concentrating the mixture under reduced pressure was performed twice. The resultant concentrated residue was purified by column chromatography on silica gel, thereby obtaining 236 mg (yield: 69%) of 1,1'-ethylenedi(hexahydro-1,4-diazepine) as a colorless oil.

In accordance with the same process as in Example 1, the title compound (115 mg; yield: 70%) was obtained as a colorless amorphous powder from (E,E)-5-(3,5-dimethoxy-4-isopropoxyphenyl)-2,4-pentadienoic acid (147 mg; 0.51 mmol) and 1,1'-ethylenedi(hexahydro-1,4-diazepine) (48 mg; 0.21 mmol) synthesized by the above process.

$^1$H-NMR (DMSO-$d_6$, 120° C.) δ: 1.20(d,J=6.2 Hz,12H), 1.76(br dddd,J=5.9,5.9,5.9,5.9 Hz,4H), 2.59(s,4H), 2.61–2.67(m,4H), 2.70–2.76(m,4H), 3.52–3.61(m,8H), 3.79 (s,12H), 4.33(qq,J=6.2,6.2 Hz,2H), 6.58(d,J=14.6 Hz,2H), 6.80(s,4H), 6.81(d,J=15.4 Hz,2H), 6.96(dd,J=15.4,10.7 Hz,2H), 7.21(dd,J=14.6,10.7 Hz,2H).

Example 23

Preparation of 1,1'-trimethylenedi[4-[4-(3,4,5-trimethoxyphenyl)benzoyl]hexahydro-1,4-diazepine] dihydrochloride

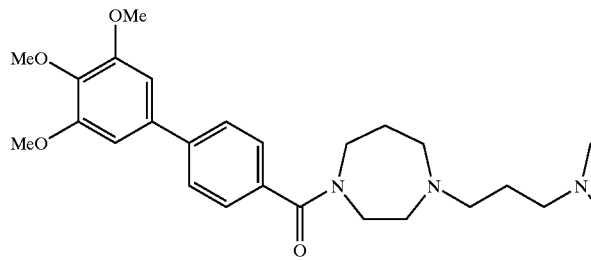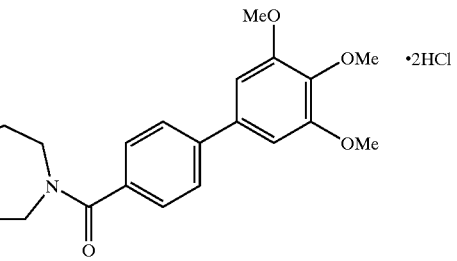

Potassium carbonate (0.50 g; 3.6 mmol) was added to a solution in water (1 ml) of 1,1'-trimethylenedi(hexahydro-1,4-diazepine) tetrahydrochloride (540 mg; 1.4 mmol) synthesized in accordance with the same process as in Referential Example 1. The mixture was stirred at room temperature for 15 minutes and concentrated under reduced pressure. A process of adding ethanol (10 ml) to the residue and concentrating the mixture under reduced pressure was conducted twice. The resultant concentrated residue was purified by column chromatography on silica gel, thereby obtaining 323 mg (yield: 96%) of 1,1'-trimethylenedi(hexahydro-1,4-diazepine) as a colorless oil.

In accordance with the same process as in Example 1, 1,1'-trimethylenedi[4-[4-(3,4,5-trimethoxyphenyl)benzoyl] hexahydro-1,4-diazepine] (105 mg; yield: 78%) was obtained as a colorless oil from 4-(3,4,5-trimethoxyphenyl)benzoic acid (118 mg; 0.41 mmol) and 1,1'-trimethylenedi(hexahydro-1,4-diazepine) (42 mg; 0.17 nmnol) synthesized by the above process.

Concentrated hydrochloric acid (0.025 ml; 0.30 mmol) was added to a solution of 1,1'-trimethylenedi[4-[4-(3,4,5-trimethoxyphenyl)benzoyl]hexahydro-1,4-diazepine](46 mg; 0.060 mmol) in ethanol (5 ml) and the reaction mixture was concentrated under reduced pressure. The concentrated residue was suspended in diethyl ether and collected by filtration to obtain the title compound as a colorless crystalline powder.

Melting point: 259° C. (decomposition).

$^1$H-NMR (data of free base of the title compound) (DMSO-$d_6$, 120° C.) δ: 1.57(tt,J=6.8,6.8 Hz,2H), 1.70–1.82 (m,4H), 2.52(t,J=6.8 Hz,4H), 2.61–2.75(m,8H), 3.48–3.61 (m,8H), 3.76(s,6H), 3.87(s,12H), 6.92(s,4H), 7.40(d,J=8.3 Hz,4H), 7.67(d,J=8.3 Hz,4H).

Example 24

Preparation of 1,1'-octamethylenedi[4-[(E,E)-5-(3,4,5-trimethoxyphenyl)-2,4-pentadienoyl]hexahydro-1,4-diazepine]dihydrochloride

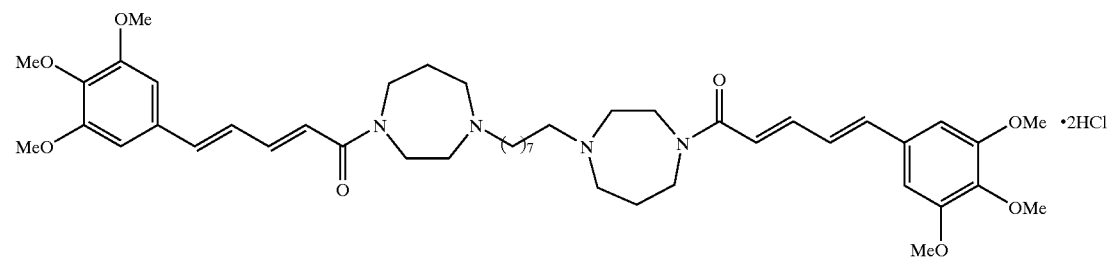

In accordance with the same process as in Example 7, 1,1'-octamethylenedi[4-[(E,E)-5-(3,4,5-trimethoxyphenyl)-2,4-pentadienoyl]hexahydro-1,4-diazepine] (96 mg; yield:

60%) was obtained as a colorless oil from (E,E)-5-(3,4,5-trimethoxyphenyl)-2,4-pentadienoic acid (116 mg; 0.44 mmol) and 1,1'-octamethylenedi(hexahydro-1,4-diazepine) (91 mg; 0.20 mmol) synthesized by a process similar to the process of Referential Example 1.

Concentrated hydrochloric acid (0.030 ml; 0.36 mmol) was added to a solution of 1,1'-octamethylenedi[4-[(E,E)-5-(3,4,5-trimethoxyphenyl)-2,4-pentadienoyl]hexahydro-1,4-diazepine] (76 mg; 0.095 mmol) in ethanol (5 ml) and the reaction mixture was concentrated under reduced pressure.

A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.20–1.45(m,8H), 1.60–1.80(m,4H), 1.95–2.40(m,8H), 2.95–3.10(m,4H), 2.10–3.60(m,4H), 3.60–3.75(m,4H), 3.72(s,6H), 3.80–3.82 (m,4H), 3.82(s,12H), 6.61(d,J=14.6 Hz,2H), 6.81(s,4H), 6.86(d,J=15.6 Hz,2H), 6.98(dd,J=15.6,10.4 Hz,2H), 7.26 (dd,J=14.6,10.4 Hz,2H).

Example 25

Preparation of 1,1'-bis[(E)-3-(3,4-dihydro-6,7,8-trimethoxy-2-naphthyl)-2-propenoyl]-4,4'-bipiperidine

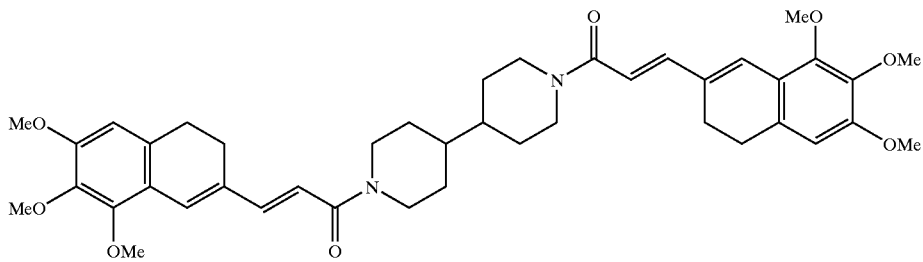

In accordance with the same process as in Example 7, crude crystals were obtained from (E)-3-(3,4-dihydro-6,7,8-trimethoxy-2-naphthyl)-2-propenoic acid (160 mg; 0.55 mmol) and 4,4'-bipiperidine dihydrochloride (60 mg; 0.25 mmol). The crude crystals thus obtained were recrystallized from chloroform-diethyl ether to obtain 99 mg (yield: 56%) of the title compound as a pale yellow crystalline powder.

Melting point: 253–256° C.

$^1$H-NMR (DMSO-$d_6$, 120° C.) δ: 1.00–1.20(m,4H), 1.40–1.50(m,2H), 1.60–1.75(m,4H), 2.50–3.00(m,8H), 3.74 (s,6H), 3.81(s,12H), 4.25–4.35(m,8H), 6.51(d,J=15.0 Hz,2H), 6.63(s,2H), 6.86(s,2H), 7.24(d,J=15.0 Hz,2H).

Example 26

Preparation of 1,1'-bis[(E)-3-(3-quinolyl)-2-propenoyl]-4,4'-bipiperidine

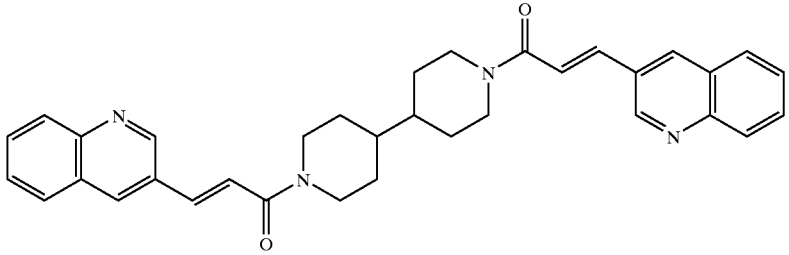

In accordance with the same process as in Example 1, crude crystals (92 mg; yield: 46%) were obtained from (E)-3-(3-quinolyl)-2-propenoic acid hydrochloride (194 mg; 0.82 mmol) and 4,4'-bipiperidine dihydrochloride (91 mg; 0.38 mmol). The crude crystals thus obtained were suspended in chloroform-diethyl ether and collected by filtration to obtain the title compound as a colorless crystalline powder.

Melting point: 270° C. or higher.

$^1$H-NMR [CD$_3$OD-CDCl$_3$ (1:5)] δ: 1.22–1.41(m,4H), 1.44–1.58(m,2H), 1.83–2.00(m,4H), 2.73(br dd,J=12.5,12.5 Hz,2H), 3.20(br dd,J=12.5,12.5 Hz,2H), 4.30(br d,J=12.5 Hz,2H), 4.77(br d,J=12.5 Hz,2H), 7.24(d,J=15.6 Hz,2H), 7.64(br dd,J=8.4,6.7 Hz,2H), 7.77(d,J=15.6 Hz,2H), 7.79(br dd,J=8.4,6.7 Hz,2H), 7.92(br d,J=8.4 Hz,2H), 8.08(br d,J= 8.4 Hz,2H), 8.36(s,2H), 9.08(s,2H).

Example 27

Preparation of 1,3-bis[1-[(E)-3-(5,6-dimethoxy-1,1-dimethyl-2-indenyl)-2-propenoyl]-4-piperidinyl] propane

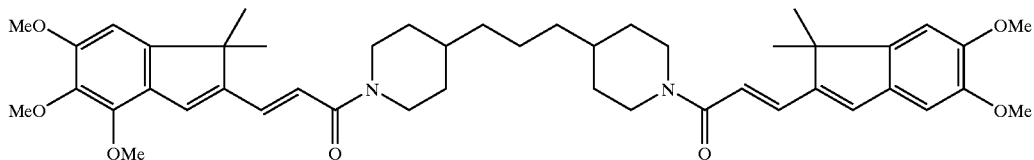

In accordance with the same process as in Example 7, crude crystals were obtained from (E)-3-(5,6-dimethoxy-1,1-dimethyl-2-indenyl)-2-propenoic acid (33 mg; 0.12 mmol) and 1,3-bis(4-peridinyl)propane (11 mg; 0.053 mmol). The crude crystals thus obtained were recrystallized from chloroform-diethyl ether to obtain 16 mg (yield: 42%) of the title compound as a pale yellow crystalline powder.

Example 29

Preparation of 1,3-bis[1-[4-(3,4,5-trimethoxyphenyl)benzoyl]-4-piperidinyl]-2-(dimethylamino)propane hydrochloride

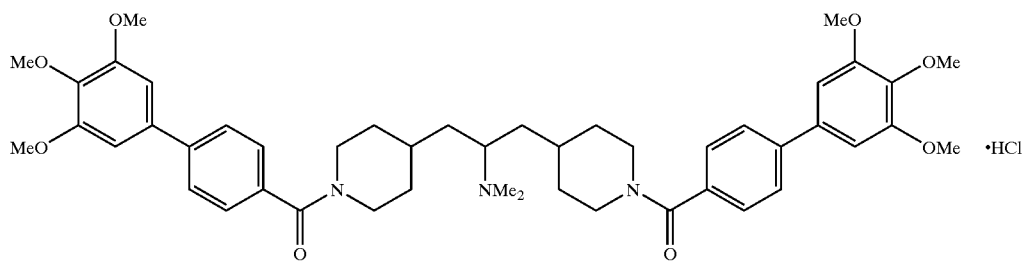

Melting point: 192–194° C.

$^1$H-NMR (DMSO-$d_6$, 120° C.) δ: 1.05–1.15(m,4H), 1.20–1.30(m,6H), 1.31(s,12H), 1.45–1.60(m,2H), 1.70–1.80(m,4H), 2.80–3.00(m,4H), 3.76(s,6H), 3.82(s,6H), 4.15–4.25(m,4H), 6.67(d,J=15.9 Hz,2H), 6.99(s,4H), 7.06(s,2H), 7.27(d,J=15.9 Hz,2H).

Example 28

Preparation of 1,3-bis[1-[5-(3,4,5-trimethoxyphenyl)-3-pyridylcarbonyl]-4-piperidinyl]propane

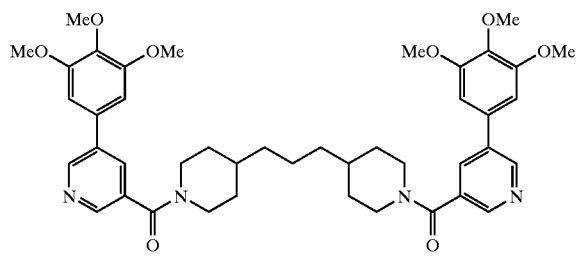

In accordance with the same process as in Example 7, the title compound (28 mg; yield: 68%) was obtained as a colorless crystalline powder from 5-(3,4,5-trimethoxyphenyl)-3-pyridinecarboxylic acid (34 mg; 0.12 mmol) and 1,3-bis(4-piperidinyl)propane (12 mg; 0.055 mmol).

$^1$H-NMR (DMSO-$d_6$, 120° C.) δ: 1.10–1.40(m,10H), 1.49–1.64(m,2H), 1.65–1.75(m,4H), 2.93–3.02(m,4H), 3.76(s,6H), 3.88(s,12H), 3.92–4.08(m,4H), 6.97(s,4H), 7.97(dd, J=2.1,2.1 Hz,2H), 8.49(d,J=2.1 Hz,2H), 8.89(d,J=2.1 Hz,2H).

A 4N hydrogen chloride in ethyl acetate (1 ml; 4 mmol) was added to a solution in ethyl acetate (0.5 ml) of 1,3-bis(1-tert-butoxycarbonyl-4-piperidinyl)-2-(dimethylamino)propane (132 mg; 0.29 mmol) synthesized by the process described in Referential Example 4, and the mixture was stirred at room temperature for 30 minutes. The reaction mixture was concentrated under reduced pressure to obtain crude crystals of 1,3-bis(4-piperidinyl)-2-(dimethylamino)propane trihydrochoride.

In accordance with the same process as in Example 7, 1,3-bis[1-[4-(3,4,5-trimethoxyphenyl)benzoyl]-4-piperidinyl]-2-(dimethylamino)propane (189 mg; yield: 82%) was obtained as a colorless oil from 4-(3,4,5-trimethoxyphenyl)benzoic acid (167 mg; 0.58 mmol) and the crude crystals of 1,3-bis(4-piperidinyl)-2-(dimethylamino)propane trihydrochoride synthesized by the above process.

Concentrated hydrochloric acid (0.060 ml; 0.72 mmol) was added to a solution of 1,3-bis[1-[4-(3,4,5-trimethoxyphenyl)benzoyl]-4-piperidinyl]-2-(dimethylamino)propane (189 mg; 0.24 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.15–1.25(m,4H), 1.40–1.50(m,2H), 1.70–1.85(m,8H), 2.69(s,6H), 2.70–3.10(m,4H), 3.20(m,1H), 3.76(s,6H), 3.87(s,12H), 4.00–4.10(m,4H), 6.92(s,4H), 7.41(d,J=8.3 Hz,4H), 7.68(d,J=8.3 Hz,4H).

Example 30

Preparation of 1,3-bis[1-[4-methyl-3-(3,4,5-trimethoxyphenyl)benzoyl]-4-piperidinyl]-2-(dimethylamino)propane hydrochloride

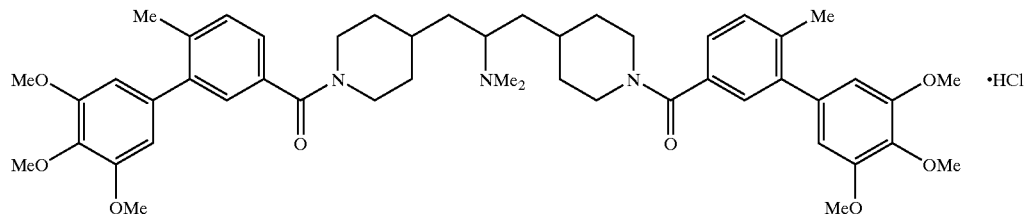

A 4N hydrogen chloride in ethyl acetate (1 ml; 4 mmol) was added to a solution in ethyl acetate (0.5 ml) of 1,3-bis(1-tert-butoxycarbonyl-4-piperidinyl)-2-(dimethylamino)propane (84 mg; 0.19 mmol) synthesized by the process described in Referential Example 4, and the mixture was stirred at room temperature for 30 minutes. The reaction mixture was concentrated under reduced pressure to obtain crude crystals of 1,3-bis(4-piperidinyl)-2-(dimethylamino)propane trihydrochoride.

In accordance with the same process as in Example 7, 1,3-bis[1-[4-methyl-3-(3,4,5-trimethoxyphenyl)benzoyl]-4-piperidinyl]-2-(dimethylamino)propane (53 mg; yield: 35%) was obtained as a colorless oil from 4-methyl-3-(3,4,5-trimethoxyphenyl)benzoic acid (112 mg; 0.37 mmol) and the crude crystals of 1,3-bis(4-piperidinyl)-2-(dimethylamino)propane trihydrochoride synthesized by the above process.

Concentrated hydrochloric acid (0.020 ml; 0.24 mmol) was added to a solution of 1,3-bis[1-[4-methyl-3-(3,4,5-trimethoxyphenyl)benzoyl]-4-piperidinyl]-2-(dimethylamino)propane (53 mg; 0.064 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.10–1.25(m,4H), 1.41–1.45(m,2H), 1.65–1.80(m,8H), 2.28(s,6H), 2.67(br s,6H), 2.80–3.00(m,4H), 3.25(m,1H), 3.76(s,6H), 3.80(s,12H), 4.00–4.10(m,4H), 6.57(s,4H), 7.18(d,J=1.7 Hz,2H), 7.23(dd,J=7.8,1.7 Hz,2H), 7.31(d,J=7.8 Hz,2H).

Example 31

Preparation of 1,3-bis[1-[(E)-5-(3,4,5-trimethoxyphenyl)-2-penten-4-ynoyl]-4-piperidinyl]-2-(dimethylamino)propane hydrochloride

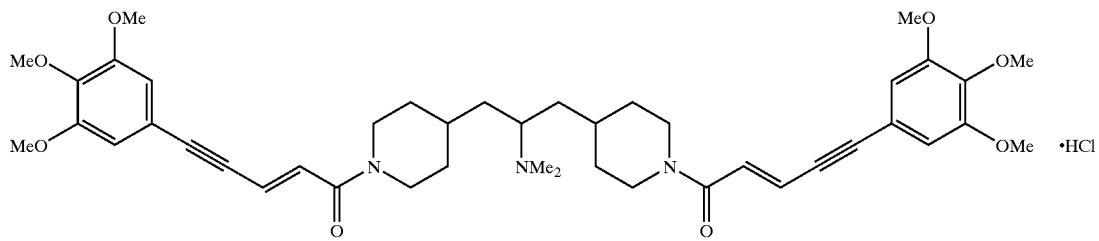

A 4N hydrogen chloride in ethyl acetate (1 ml; 4 mmol) was added to a solution in ethyl acetate (0.5 ml) of 1,3-bis(1-tert-butoxycarbonyl-4-piperidinyl)-2-(dimethylamino)propane (135 mg; 0.30 mmol) synthesized by the process described in Referential Example 4, and the mixture was stirred at room temperature for 30 minutes. The reaction mixture was concentrated under reduced pressure to obtain crude crystals of 1,3-bis(4-piperidinyl)-2-(dimethylamino)propane trihydrochoride.

In accordance with the same process as in Example 7, 1,3-bis[1-[(E)-5-(3,4,5-trimethoxyphenyl)-2-penten-4-ynoyl]-4-piperidinyl]-2-(dimethylamino)propane (104 mg; yield: 47%) was obtained as a colorless oil from (E)-5-(3,4,5-trimethoxyphenyl)-2-penten-4-ynoic acid (157 mg; 0.60 mmol) and the crude crystals of 1,3-bis(4-piperidinyl)-2-(dimethylamino)propane trihydrochoride synthesized by the above process.

Concentrated hydrochloric acid (0.035 ml; 0.42 mmol) was added to a solution of 1,3-bis[1-[(E)-5-(3,4,5trimethoxyphenyl)-2-penten-4-ynoyl]-4-piperidinyl]-2-(dimethylamino)propane (104 mg; 0.14 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.00–1.20(m,4H), 1.40–1.50(m,2H), 1.70–1.80(m,8H), 2.68(s,6H), 2.80–3.00 (m,4H), 3.25(m,1H), 3.74(s,6H), 3.80(s,12H), 4.15–4.25(m, 4H), 6.73(d,J=15.4 Hz,2H), 6.77(s,4H), 6.99(d,J=15.4 Hz,2H).

Example 32

Preparation of 1,3-bis[1-[4-(3,4,5-trimethoxyphenyl) benzoyl]-4-piperidinyl]-2-[(dimethylamino)methyl] propane hydrochloride

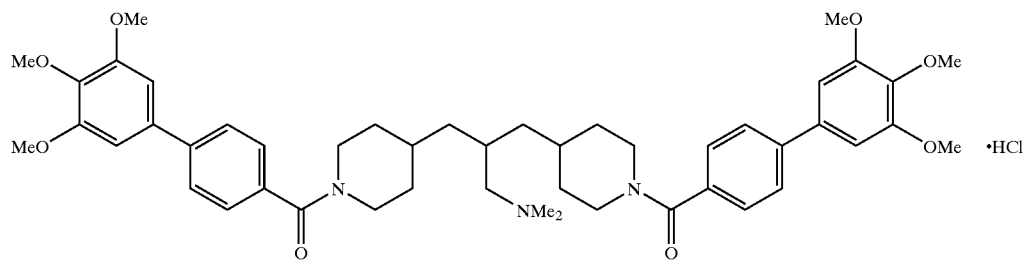

A 4N hydrogen chloride in ethyl acetate (1 ml; 4 mmol) was added to a solution in ethyl acetate (0.5 ml) of 1,3-bis (1-tert-butoxycarbonyl-4-piperidinyl)-2-[(dimethylamino) methyl]propane (67 mg; 0.14 mmol) synthesized by the process described in Referential Example 5, and the mixture was stirred at room temperature for 30 minutes. The reaction mixture was concentrated under reduced pressure to obtain crude crystals of 1,3-bis(4-piperidinyl)-2-[(dimethylamino) methyl]propane trihydrochoride.

In accordance with the same process as in Example 7, 1,3-bis[1-[4-(3,4,5-trimethoxyphenyl)benzoyl]-4-piperidinyl]-2-[(dimethylamino)methyl]propane (62 mg; yield: 54%) was obtained as a colorless oil from 4-(3,4,5-trimethoxyphenyl)benzoic acid (157 mg; 0.60 mmol) and the crude crystals of 1,3-bis(4-piperidinyl)-2-[(dimethylamino)methyl]propane trihydrochoride synthesized by the above process.

Concentrated hydrochloric acid (0.020 ml; 0.24 mmol) was added to a solution of 1,3-bis[1-[4-(3,4,5-trimethoxyphenyl)benzoyl]-4-piperidinyl]-2-

[(dimethylamino)methyl]propane (62 mg) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.00–1.45(m,8H), 1.65–1.75(m,7H), 2.74(s,6H), 2.80–3.00(m,6H), 3.75(s,6H), 3.87(s,12H), 4.00–4.10(m,4H), 6.92(s,4H), 7.41(d,J=8.3 Hz,4H), 7.68(d,J=8.3 Hz,4H).

Example 33

Preparation of 1,3-bis[1-[(E)-5-(3,4,5-trimethoxyphenyl)-2-penten-4-ynoyl]-4-piperidinyl]-2-[(dimethylamino)methyl]propane hydrochloride

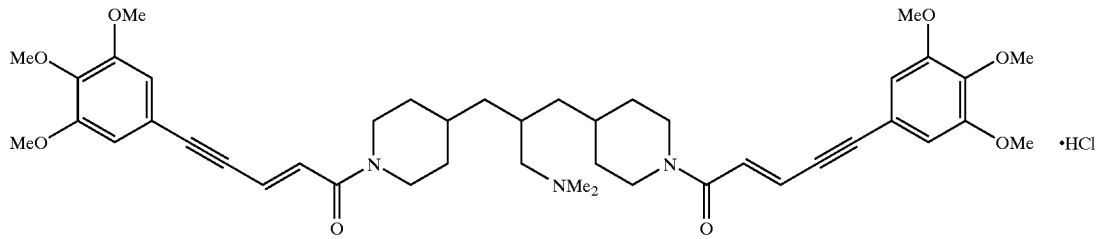

A 4N hydrogen chloride in ethyl acetate (1 ml; 4 mmol) was added to a solution in ethyl acetate (0.5 ml) of 1,3-bis (1-tert-butoxycarbonyl-4-piperidinyl)-2-[(dimethylamino) methyl]propane (92 mg; 0.20 mmol) synthesized by the process described in Referential Example 5, and the mixture was stirred at room temperature for 30 minutes. The reaction mixture was concentrated under reduced pressure to obtain crude crystals of 1,3-bis(4-piperidinyl)-2-[(dimethylamino) methyl]propane trihydrochoride.

In accordance with the same process as in Example 7, 1,3-bis[1-[(E)-5-(3,4,5-trimethoxyphenyl)-2-penten-4-ynoyl]-4-piperidinyl]-2-[(dimethylamino)methyl]propane (46 mg; yield: 31%) was obtained as a pale yellow oil from (E)-5-(3,4,5-trimethoxyphenyl)-2-penten-4-ynoic acid (105 mg; 0.40 mmol) and the crude crystals of 1,3-bis(4-piperidinyl)-2-[(dimethylamino)methyl]propane trihydrochoride synthesized by the above process.

Concentrated hydrochloric acid (0.020 ml; 0.24 mmol) was added to a solution of 1,3-bis[1-[(E)-5-(3,4,5-trimethoxyphenyl)-2-penten-4-ynoyl]-4-piperidinyl]-2-[(dimethylamino)methyl]propane (46 mg; 0.061 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-d$_6$, 120° C.) (no NH$^+$ proton of the ammonium salt was observed) δ: 1.20–1.40(m,8H), 1.60–1.80(m,7H), 2.75(s,6H), 2.80–3.00(m,6H), 3.74(s,6H), 3.80(s,12H), 4.10–4.20(m,4H), 6.72(d,J=15.4 Hz,2H), 6.77 (s,4H), 6.98(d,J=15.4 Hz,2H).

Example 34

Preparation of 1,3-bis[1-[(E)-5-(3,4,5-trimethoxyphenyl)-2-penten-4-ynoyl]-4-piperidinyl]-2-propanecarboxylic acid

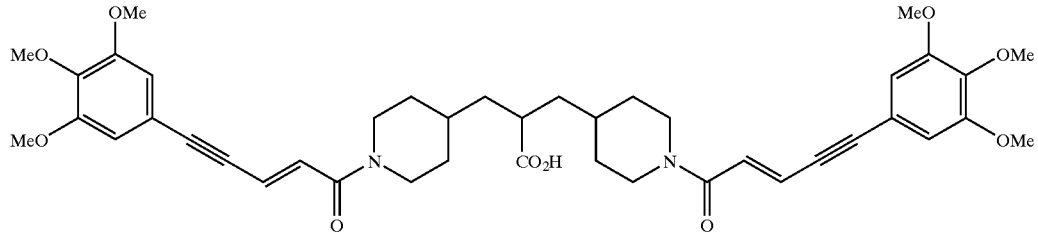

$^1$H-NMR (DMSO-d$_6$, 120° C.) (no OH proton of the carboxyl group was observed) δ: 1.00–1.90(m,14H), 2.40–3.00(m,5H), 3.74(s,6H), 3.80(s,12H), 4.10–4.20(m, 4H), 6.71(d,J=15.4 Hz,2H), 6.78(s,4H), 6.97(d,J=15.4 Hz,2H).

Example 35

Preparation of N,N-bis[[1-[4-(3,4,5-trimethoxyphenyl)benzoyl]-4-piperidinyl]methyl] methylamine hydrochloride

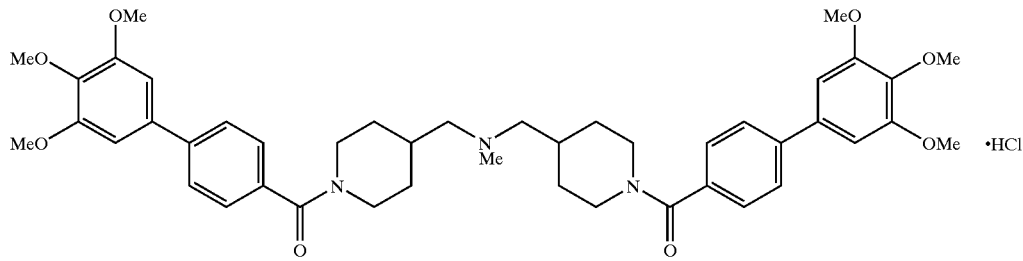

In accordance with the same process as in Example 7, methyl 1,3-bis[1-[(E)-5-(3,4,5-trimethoxyphenyl)-2-penten-4-ynoyl]-4-piperidinyl]-2-propanecarboxylate (136 mg; yield: 88%) was obtained as a colorless oil from (E)-5-(3,4,5-trimethoxyphenyl)-2-penten-4-ynoic acid (116 mg; 0.44 mmol) and methyl 2,2-bis[(4-piperidinyl)methyl]acetate dihydrochloride (70 mg; 0.21 mmol) synthesized by the process described in Referential Example 3.

A 5N aqueous sodium hydroxide (2 ml; 10 mmol) was added to a solution in methanol (2 ml) of methyl 1,3-bis[1-[(E)-5-(3,4,5-trimethoxyphenyl)-2-penten-4-ynoyl]-4-piperidinyl]-2-propanecarboxylate (136 mg; 0.18 mmol) synthesized by the above process, and the mixture was stirred for 1 hour in a bath controlled at 65° C. The reaction mixture was made acidic by addition of 1N hydrochloric acid and extracted with chloroform. The organic layer was washed with saturated brine, dried over anhydrous sodium sulfate and then concentrated under reduced pressure. The resultant crude oil was purified by column chromatography on silica gel, thereby obtaining 46 mg (yield: 35%) of the title compound as a pale yellow amorphous powder.

In accordance with the same process as in Example 7, N,N-bis[[1-[4-(3,4,5-trimethoxyphenyl)benzoyl]-4-piperidinyl]methyl]methylamine (144 mg; yield: 94%) was obtained as a colorless oil from 4-(3,4,5-trimethoxyphenyl) benzoic acid (126 mg; 0.44 mmol) and N,N-bis[(4-piperidinyl)methyl]methylamine trihydrochloride (67 mg; 0.20 mmol) synthesized by the process described in Referential Example 6.

Concentrated hydrochloric acid (0.045 ml; 0.54 mmol) was added to a solution of N,N-bis[[1-[4-(3,4,5-trimethoxyphenyl)benzoyl]-4-piperidinyl]methyl] methylamine (142 mg; 0.18 mmol) in ethanol (5 ml) and the reaction mixture was concentrated under reduced pressure. A process of adding ethanol (10 ml) to the residue and concentrating the mixture under reduced pressure was performed twice to obtain the title compound as a colorless amorphous powder.

$^1$H-NMR (DMSO-d$_6$, 120° C.) (no NH$^+$ proton of the ammonium salt was observed) δ: 1.35–1.40(m,4H), 1.80–2.00(m,4H), 2.10–2.20(m,2H), 2.70–3.30(m,11H), 3.75(s,6H), 3.86(s,12H), 4.00–4.15(m,4H), 6.91(s,4H), 7.41 (d,J=8.2 Hz,4H), 7.67(d,J=8.2 Hz,4H).

Example 36

Preparation of N,N-bis[[1-[(E)-3-(6,7,8-trimethoxy-2-naphthyl)-2-propenoyl]-4-piperidinyl]methyl] methylamine hydrochloride

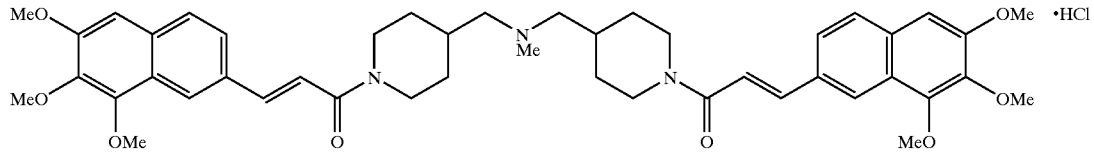

In accordance with the same process as in Example 7, N,N-bis[[1-[(E)-3-(6,7,8-trimethoxy-2-naphthyl)-2-propenoyl]-4-piperidinyl]methyl]methylamine (57 mg; yield: 87%) was obtained as a colorless oil from (E)-3-(6,7,8-trimethoxy-2-naphthyl)-2-propenoic acid (50 mg; 0.17 mmol) and N,N-bis[(4-piperidinyl)methyl]methylamine trihydrochloride (29 mg; 0.086 mmol) synthesized by the process described in Referential Example 6.

Concentrated hydrochloric acid (0.020 ml; 0.24 mmol) was added to a solution of N,N-bis[[1-[(E)-3-(6,7,8-trimethoxy-2-naphthyl)-2-propenoyl]-4-piperidinyl]methyl]-methylamine (57 mg; 0.074 mmol) in ethanol (5 ml) and the reaction mixture was concentrated under reduced pressure. A process of adding ethanol (10 ml) to the residue and concentrating the mixture under reduced pressure was performed twice to obtain the title compound as a pale yellow amorphous powder.

$^1$H-NMR (DMSO-$d_6$, 120° C.) (no NH$^+$ proton of the ammonium salt was observed) δ: 1.20–1.32(m,4H), 1.80–2.15(m,6H), 2.70–3.10(m,8H), 2.78(br s,3H), 3.88(s,6H), 3.93(s,6H), 4.00(s,6H), 4.25–4.37(m,4H), 7.13(d,J=15.4 Hz,2H), 7.14(s,2H), 7.58(d,J=15.4 Hz,2H), 7.71(dd,J=8.5,1.5 Hz,2H), 7.74(d,J=8.5 Hz,2H), 8.04(br s,2H).

Example 37

Preparation of N,N'-bis[1-[4-(3,4,5-trimethoxyphenyl)benzoyl)-4-piperidinyl]-N,N'-dimethylethylenediamine dihydrochloride In accordance with the same process as in Example 1, N,N'-bis[1-[4-(3,4,5-trimethoxyphenyl)benzoyl]-4-piperidinyl]-N,N'-dimethylethylenediamine (159 mg; yield: 87%) was obtained as a colorless oil from 4-(3,4,5-trimethoxyphenyl)benzoic acid (173 mg; 0.60 mmol) and N,N'-bis(4-piperidinyl)-N,N'-dimethylethylenediamine tetrahydrochloride (92 mg; 0.23 mmol) synthesized by the process described in Referential Example 7.

Concentrated hydrochloric acid (0.030 ml; 0.36 mmol) was added to a solution of N,N'-bis[1-[4-(3,4,5-trimethoxyphenyl)benzoyl]-4-piperidinyl]-N,N'-dimethylethylenediamine (60 mg; 0.076 mmol) in ethanol (5 ml) and the reaction mixture was concentrated under reduced pressure. The concentrated residue was suspended in diethyl ether and collected by filtration to obtain the title compound as a colorless crystalline powder.

Melting point: 263° C. (decomposition).

$^1$H-NMR (data of free base of the title compound) (DMSO-$d_6$, 120° C.) δ: 1.37–1.50(m,4H), 1.72–1.80(m,4H), 2.26(s,6H), 2.55(s,4H), 2.59–2.69(m,2H), 2.85–2.99(m,4H), 3.77(s,6H), 3.88(s,12H), 4.04–4.15(m,4H), 6.93(s,4H), 7.43 (d,J=8.5 Hz,4H), 7.68(d,J=8.5 Hz,4H).

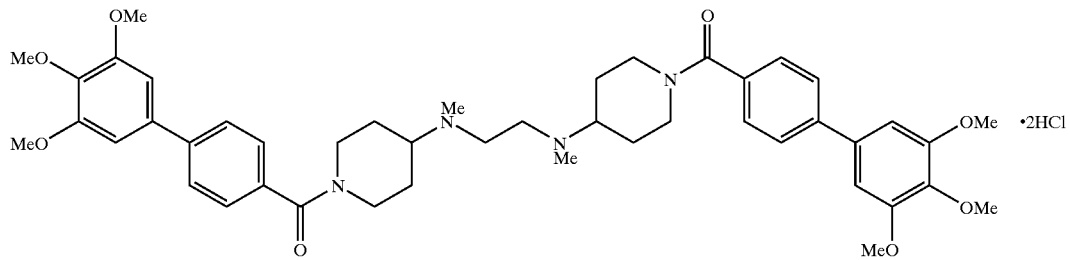

Example 38

Preparation of N,N'-bis[1-[4-fluoro-3-(3,4,5-trimethoxyphenyl)benzoyl]-4-piperidinyl]-N,N'-dimethylethylenediamine

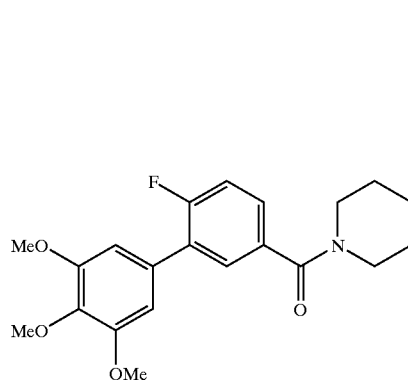

In accordance with the same process as in Example 1, the title compound (49 mg; yield: 83%) was obtained as a colorless amorphous powder from 4-fluoro-3-(3,4,5-trimethoxyphenyl)benzoic acid (59 mg; 0.18 mmol) and N,N'-bis(4-piperidinyl)-N,N'-dimethylethylenediamine tetrahydrochloride (29 mg; 0.072 mmol) synthesized by the process described in Referential Example 7.

$^1$H-NMR (DMSO-$d_6$, 120° C.) δ: 1.36–1.49(m,4H), 1.69–1.78(m,4H), 2.31(s,6H), 2.52(s,4H), 2.57–2.66(m,2H), 2.86–2.99(m,4H), 3.76(s,6H), 3.83(s,12H), 4.00–4.13(m, 4H), 6.82(s,4H), 7.27(dd,J=8.5, $^3J_{HF}$=10.9 Hz,2H), 7.35 (ddd,J=8.5,2.3,$^4J_{HF}$=4.9 Hz,2H), 7.50(dd,J=2.3,$^4J_{HF}$=7.6 Hz,2H).

Example 39

Preparation of 1,4-bis[[1-[4-(3,4,5-trimethoxyphenyl)benzoyl]-4-piperidinyl]methyl]piperazine dihydrochloride In accordance with the same process as in Example 7, 1,4-bis[[1-[4-(3,4,5-trimethoxyphenyl)benzoyl]-4-piperidinyl]methyl]piperazine (101 mg; yield: 82%) was obtained as a colorless oil from 4-(3,4,5-trimethoxyphenyl)benzoic acid (91 mg; 0.31 mmol) and 1,4-bis[(4-piperidinyl)methyl]piperazine tetrahydrochloride (64 mg; 0.15 mmol) synthesized by the process described in Referential Example 8.

Concentrated hydrochloric acid (0.050 ml; 0.60 mmol) was added to a solution of 1,4-bis[[1-[4-(3,4,5-trimethoxyphenyl)benzoyl]-4-piperidinyl]methyl]piperazine (100 mg; 0.12 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as colorless needles.

Melting point: 261–263° C.

$^1$H-NMR (DMSO-$d_6$, 120° C.) (no NH$^+$ proton of the ammonium salt was observed) δ: 1.15–1.35(m,4H), 1.80–1.90(m,4H), 1.97–2.10(m,2H), 2.70–2.80(m,4H), 2.80–3.40(m,12H), 3.75(s,6H), 3.86(s,12H), 3.95–4.10(m, 4H), 6.92(s,4H), 7.41(d,J=8.2 Hz,4H), 7.68(d,J=8.2 Hz,4H).

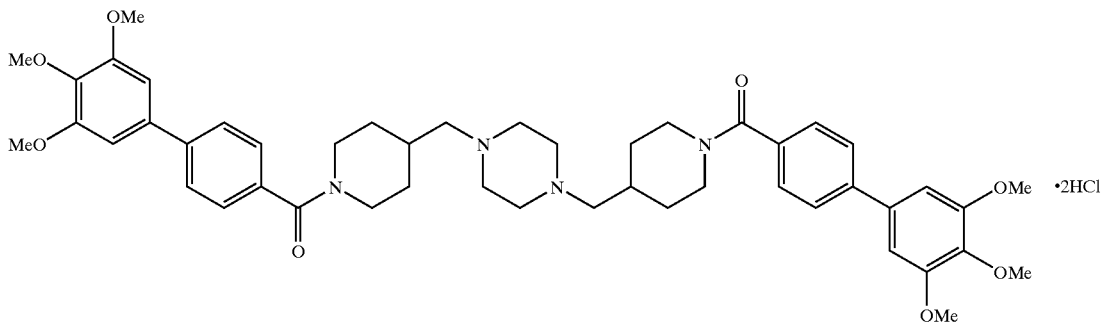

Example 40

Preparation of 1,4-bis[[1-[4-methoxy-3-(3,4,5-trimethoxyphenyl)benzoyl]-4-piperidinyl]methyl]piperazine dihydrochloride

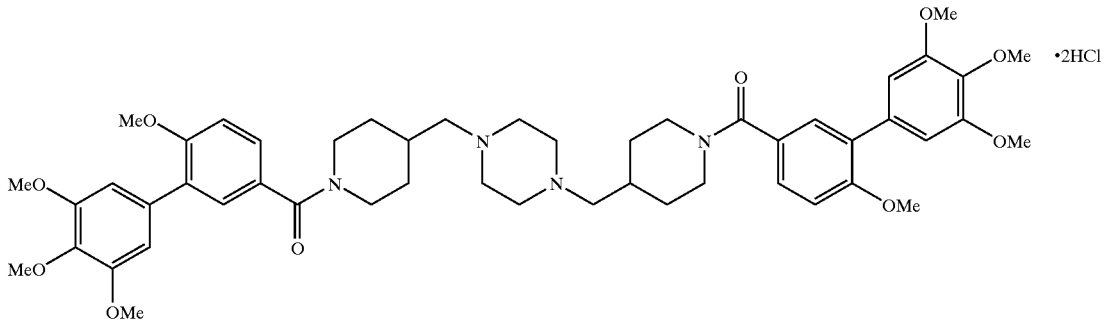

In accordance with the same process as in Example 7, 1,4-bis[[1-[4-methoxy-3-(3,4,5-trimethoxyphenyl)benzoyl]-4-piperidinyl]methyl]piperazine (81 mg; yield: 61%) was obtained as a colorless oil from 4-methoxy-3-(3,4,5-trimethoxyphenyl)benzoic acid (100 mg; 0.35 mmol) and 1,4-bis(4-piperidinyl)methyl]piperazine tetrahydrochloride (63 mg; 0.15 mmol) synthesized by the process described in Referential Example 8.

Concentrated hydrochloric acid (0.040 ml; 0.48 mmol) was added to a solution of 1,4-bis[[1-[4-methoxy-3-(3,4,5-trimethoxyphenyl)benzoyl]-4-piperidinyl]methyl]piperazine (80 mg; 0.090 mmol) in ethanol (5 ml) and the reaction mixture was concentrated under reduced pressure. After a process of adding ethanol (10 ml) to the residue and concentrating the mixture under reduced pressure was performed twice, the resultant concentrated residue was recrystallized from methanol-diethyl ether to obtain the title compound as colorless needles.

Melting point: 251–253° C.

$^1$H-NMR (DMSO-$d_6$, 120° C.) (no NH$^+$ proton of the ammonium salt was observed) δ: 1.10–1.30(m,4H), 1.75–1.85(m,4H), 1.95–2.05(m,2H), 2.55–3.40(m,16H), 3.75(s,6H), 3.81(s,12H), 3.82(s,6H), 4.00–4.15(m,4H), 6.75(s,4H), 7.11(d,J=8.2 Hz,2H), 7.30(d,J=2.1 Hz,2H), 7.33(dd, J=8.2,2.1 Hz,2H).

The thus-obtained compounds according to the present invention are shown in Tables 1 to 10.

TABLE 1

| No | A | Z | ‑N(CH$_2$)$_m$(CH$_2$)$_n$B‑ | Y | X |
|---|---|---|---|---|---|
| 1 | 3,4,5-tri(MeO)phenyl | —(CH=CH)$_2$— | piperazine | single bond | —(CH$_2$)$_2$— |
| 2 | 3,4,5-tri(MeO)phenyl | 1,4-phenylene | piperazine | single bond | —(CH$_2$)$_2$— |
| 3 | 3,4,5-tri(MeO)phenyl | —(CH=CH)$_2$— | piperazine | single bond | —(CH$_2$)$_3$— |

TABLE 1-continued
| No | A | Z | —N((CH₂)ₘ/(CH₂)ₙ)B— | Y | X |
|----|---|---|---------------------|---|---|
| 4 | 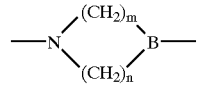 (t-Bu, OMe, Me-substituted phenyl) | —(CH=CH)₂— | 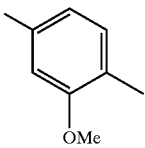 (piperazine) | single bond | —(CH₂)₃— |
15
TABLE 2
| No | A | Z | —N((CH₂)ₘ/(CH₂)ₙ)B— | Y | X |
|----|---|---|---------------------|---|---|
| 5 | 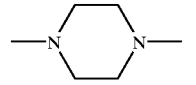 (3,4,5-triMeO-phenyl) | 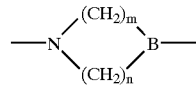 (p-phenylene) | 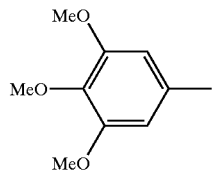 (piperazine) | single bond | —(CH₂)₃— |
| 6 | 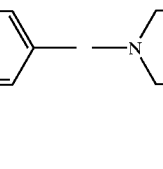 (3,4,5-triMeO-phenyl) | —C≡C—CH=CH— |  (piperazine) | single bond | —(CH₂)₃— |
| 7 | 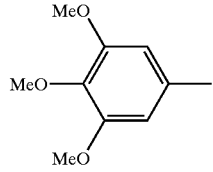 (3,4,5-triMeO-phenyl) | —C≡C— |  (piperazine) | single bond | —(CH₂)₃— |
| 8 | 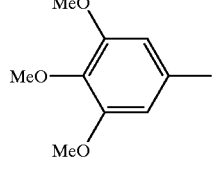 (3,4,5-triMeO-phenyl connected to 5-NO₂-2,3-diMe-phenyl) | | 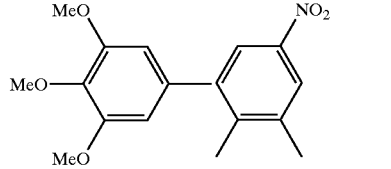 (piperazine) | single bond | —(CH₂)₃— |

TABLE 3

| No | A | Z | —N⟨(CH₂)ₘ/(CH₂)ₙ⟩B— | Y | X |
|----|---|---|---|---|---|
| 9 | 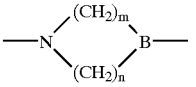 3,4,5-(MeO)₃-C₆H₂-C₆H₂(NH₂)(Me)- | | 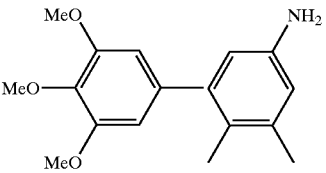 piperazine | single bond | —(CH₂)₃— |
| 10 |  4-F₃C-C₆H₄- | —(CH=CH)₂— | 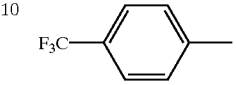 piperazine | single bond | —(CH₂)₃— |
| 11 | 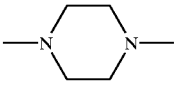 3,4,5-(MeO)₃-C₆H₂- | 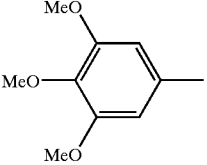 1,4-C₆H₄ |  piperazine | single bond | —(CH₂)₄— |
| 12 | 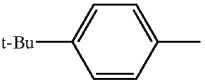 4-t-Bu-C₆H₄- | —(CH=CH)₂— |  piperazine | single bond | —(CH₂)₈— |

TABLE 4

| No | A | Z | —N⟨(CH₂)ₘ/(CH₂)ₙ⟩B— | Y | X |
|----|---|---|---|---|---|
| 13 | 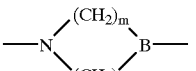 2-SMe-3-Me-pyridyl | —(CH=CH)₂— | 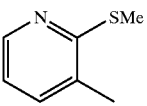 piperazine | single bond | —(CH₂)₈— |
| 14 |  3,4,5-(MeO)₃-C₆H₂- | 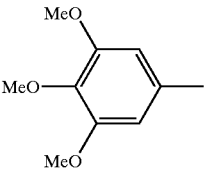 1,4-C₆H₄ |  piperazine | —CH₂— | 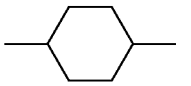 1,4-cyclohexyl |
| 15 | 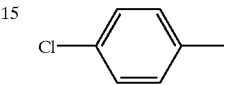 4-Cl-C₆H₄- | —(CH=CH)₂— |  piperazine | —CH₂— | 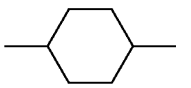 1,4-cyclohexyl |

TABLE 4-continued
| No | A | Z | —N⟨(CH₂)ₘ/(CH₂)ₙ⟩B— | Y | X |
|----|---|---|---|---|---|
| 16 | 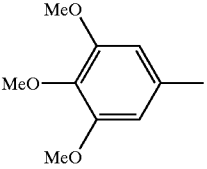 | 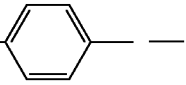 | 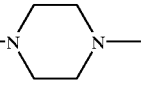 | —CH₂— | 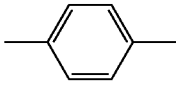 |
TABLE 5
| No | A | Z | —N⟨(CH₂)ₘ/(CH₂)ₙ⟩B— | Y | X |
|----|---|---|---|---|---|
| 17 | 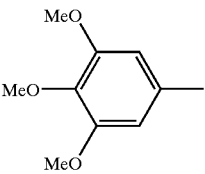 | —C≡C—CH=CH— |  | —CH₂— | 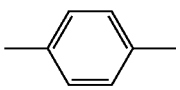 |
| 18 | 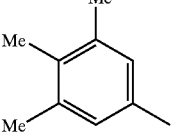 | —(CH=CH)₂— | 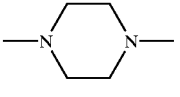 | —CH₂— | 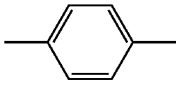 |
| 19 | 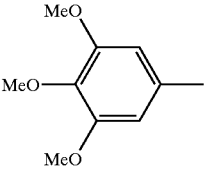 | 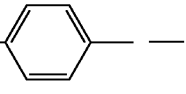 | 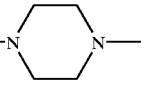 | —CH₂— | 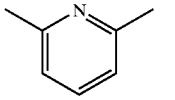 |
| 20 | 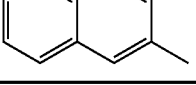 | —CH=CH— | 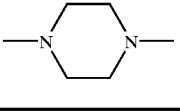 | —CH₂— | 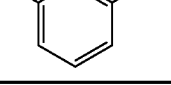 |

TABLE 6

$$-N\underset{(CH_2)_n}{\overset{(CH_2)_m}{\diagdown}}B-$$

| No | A | Z | (ring) | Y | X |
|---|---|---|---|---|---|
| 21 | 3,4,5-tri(MeO)-phenyl | -(1,4-phenylene)- | piperazine | single bond | -(1,4-phenylene)- |
| 22 | 3-MeO,4-iPrO,5-MeO-phenyl | -(CH=CH)$_2$- | 1,4-diazepane | single bond | -(CH$_2$)$_2$- |
| 23 | 3,4,5-tri(MeO)-phenyl | -(1,4-phenylene)- | 1,4-diazepane | single bond | -(CH$_2$)$_3$- |
| 24 | 3,4,5-tri(MeO)-phenyl | -(CH=CH)$_2$- | 1,4-diazepane | single bond | -(CH$_2$)$_8$- |

TABLE 7

$$-N\underset{(CH_2)_n}{\overset{(CH_2)_m}{\diagdown}}B-$$

| No | A | Z | (ring) | Y | Z |
|---|---|---|---|---|---|
| 25 | 5,6,7-tri(MeO)-tetrahydronaphthalen-2-yl | -CH=CH- | piperidine | single bond | single bond |
| 26 | quinolin-3-yl | -CH=CH- | piperidine | single bond | single bond |
| 27 | 5,6-di(MeO)-1,1,2-trimethyl-indenyl | -CH=CH- | piperidine | single bond | -(CH$_2$)$_3$- |

TABLE 7-continued
| No | A | Z | —N(CH₂)ₘ / (CH₂)ₙ B— | Y | Z |
|---|---|---|---|---|---|
| 28 | 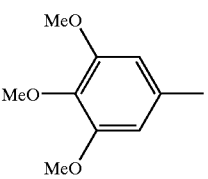 | 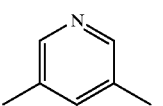 | 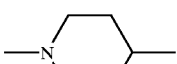 | single bond | —(CH₂)₃— |
TABLE 8
| No | A | Z | —N(CH₂)ₘ / (CH₂)ₙ B— | Y | X |
|---|---|---|---|---|---|
| 29 | 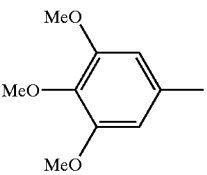 | 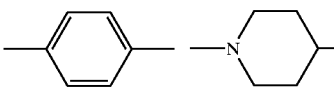 |  | single bond | 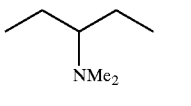 |
| 30 | 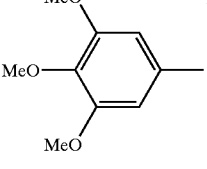 | 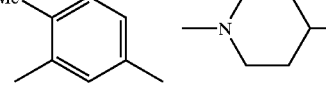 |  | single bond | 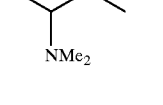 |
| 31 | 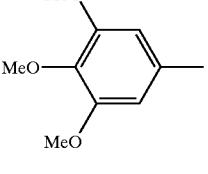 | —C≡C—CH=CH— | 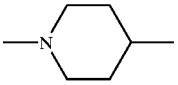 | single bond | 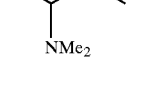 |
| 32 | 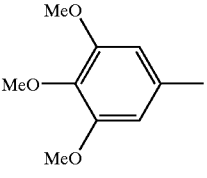 | 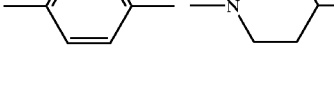 |  | single bond | 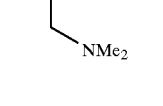 |

TABLE 9
| No | A | Z | 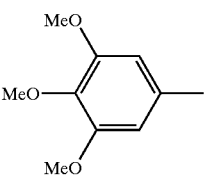 | Y | X |
|---|---|---|---|---|---|
| 33 | 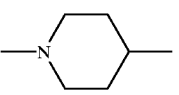 | —C≡C—CH=CH— | 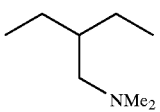 | single bond | 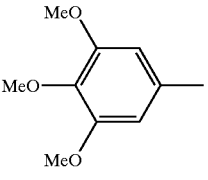 |
| 34 | 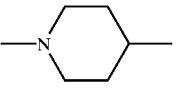 | —C≡C—CH=CH— | 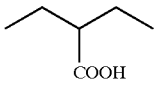 | single bond | 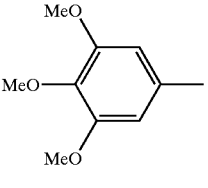 |
| 35 | 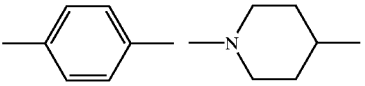 | 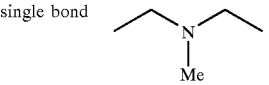 |  | single bond | 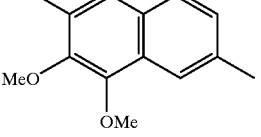 |
| 36 | 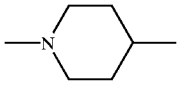 | —CH=CH— |  | single bond | 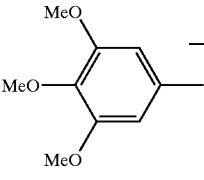 |
TABLE 10
| No | A | Z | 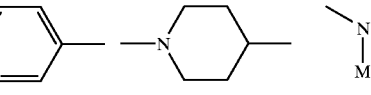 | Y | X |
|---|---|---|---|---|---|
| 37 | 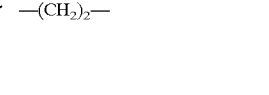 |  | 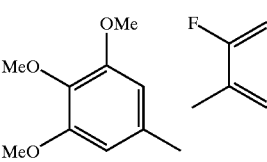 | 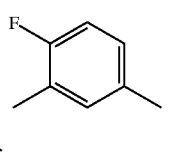 | —(CH$_2$)$_2$— |
| 38 | 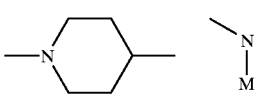 |  | | | —(CH$_2$)$_2$— |

TABLE 10-continued

| No | A | Z | —N⟨(CH₂)ₘ / (CH₂)ₙ⟩B— | Y | X |
|---|---|---|---|---|---|
| 39 | 3,4,5-tri-MeO-phenyl | -CH₂-phenylene- | piperidine-1,4-diyl | —CH₂— | piperazine-1,4-diyl |
| 40 | 3,4,5-tri-MeO-phenyl | 2-MeO-4,5-dimethyl-phenyl | piperidine-1,4-diyl | —CH₂— | piperazine-1,4-diyl |

Test Example 1

Evaluation of Inhibitory Effect on Production of IgE Antibody

A spleen was enucleated from a mouse (Balb/C, male, aged 8 weeks) and shredded in 0.3% BSA/HBSS to prepare single cells by means of a 200-mesh screen. Further, the single cells were hemolyzed by 0.75% ammonium chloride-17 mM Tris solution to prepare a splenocyte suspension ($1 \times 10^7$/ml) using RPMI 1640 medium/25 mM HEPES/0.3% BSA. After the suspension was reacted with a rat anti-mouse Thy-1,2 monoclonal antibody (product of Cedarlane Co.) at 4° C. for 1 hour, the reaction mixture was centrifuged, and the sediment cells were suspended again ($1 \times 10^7$/ml, RPMI/HEPES/BSA). After the suspension was then reacted with a low-cytotoxic rabbit complement (product of Cedarlane Co.) at 37° C. for 1 hour, killed cells were removed by specific gravity centrifugation using lympholyte M (product of Cedarlane Co.) to obtain a B cell fraction as viable cells.

After B cells (105/0.2 ml/well) were cultured for a day together with LPS (*E. coli* 026:B6, product of DIFCO Co.) using a 96-well plate, mouse IL-4 (product of Genzyme Co.) was added to conduct culture further for 7 days.

Each test agent was added on the first day of the culture, and the amount of IgE in a culture supernatant was measured by ELISA after the culture, thereby calculating out the inhibitory effect of the agent on the production of an IgE antibody. The inhibitory activities of the test agents at a concentration of $10^{-6}$ M are shown in Table 11.

TABLE 11

| Compound (Example No.) | Inhibitory effect on production of IgE (%) |
|---|---|
| 3 | 100 |
| 5 | 95 |
| 6 | 95 |
| 12 | 90 |
| 13 | 95 |
| 16 | 65 |
| 20 | 75 |
| 23 | 85 |
| 27 | 100 |

TABLE 11-continued

| Compound (Example No.) | Inhibitory effect on production of IgE (%) |
|---|---|
| 30 | 100 |
| 33 | 100 |
| 36 | 60 |
| 37 | 100 |
| 40 | 75 |

INDUSTRIAL APPLICABILITY

The cyclic amide compounds (1) according to the present invention have an inhibitory effect on the production of an IgE antibody and are hence useful as medicines for preventing and treating immunological diseases in which IgE participate, for example, various allergic immunological diseases such as asthma.

What is claimed is:

1. A compound having the formula (1):

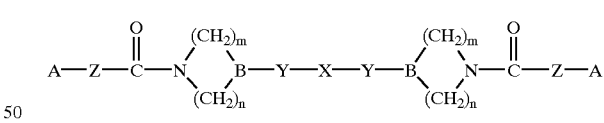

wherein:

A is indenyl, phenyl, naphthyl, dihydronaphthyl, indolyl, isoindolyl, pyridyl, quinolyl or isoquinolyl, each of which is optionally substituted by 1 to 3 substituents selected from the group consisting of hydroxyl; halogen; lower alkyl which is optionally substituted by 1 to 3 halogen; lower alkoxy; amino; monoalkylamino; dialkylamino; and lower alkylthio;

X is a single bond; lower alkylene which is optionally substituted; divalent residue of an alicyclic compound which is optionally substituted; aromatic compound which is optionally substituted; heterocyclic compound which is optionally substituted; imino which is optionally substituted; or a sulfur atom or an oxygen atom;

Y is a single bond, lower alkylene, imino or lower alkylimino;

Z is a group of the formula —CH=CH—, —C≡C—, —(CH=CH)$_2$—, —C≡C—CH=CH— or —CH=CH—C≡C—, or a divalent residue of benzene, pyridine, pyrimidine or pyrazine which is each optionally substituted;

B is a nitrogen atom; and m and n are the same or different from each other and are each independently an integer of 1 to 4;

or a salt or solvate thereof.

2. The compound of claim 1, wherein X is lower alkylene which is optionally substituted by (one or more substituents selected from the group consisting of halogen; hydroxyl; lower alkyl which is optionally substituted by amino, monoalkylamino or dialkylamino; lower alkoxy; carboxyl; lower alkoxy carbonyl; amino; alkylamino; dialkylamino; nitro; cyano; aralkyl, and imino which is optionally substituted by lower alkyl.

3. The compound of claim 1, wherein X is a divalent residue of an alicyclic compound having 5 to 8 carbon atoms, which is optionally substituted by one or more substituents selected from the group consisting of halogen; hydroxyl; lower alkyl which is optionally substituted by amino, monoalkylamino or dialkylamino; lower alkoxy; carboxyl; lower alkoxycarbonyl; amino; alkylamino; dialkylamino; nitro; cyano and aralkyl.

4. The compound of claim 1, wherein X is phenylene which is optionally substituted by one or more substituents selected from the group consisting of halogen; hydroxyl; lower alkyl which is optionally substituted by amino, monoalkylamino or dialkylamino; lower alkoxy; carboxyl; lower alkoxycarbonyl; amino; alkylamino; dialkylamino; nitro; cyarto and aralkyl.

5. The compound of claim 1, wherein X is a divalent residue of a heterocyclic compound, which is pyridine, pyrrolidine, piperidine, piperizine or homopiperizine which is each optionally substituted by one or more substituents selected from the group consisting, of halogen; hydroxyl; lower alkyl which is optionally substituted by amino, monoalkylamino or dialkylamino; lower alkoxy; carboxyl; lower alkoxycarbonyl; amino; alkylamino; dialkylamino; nitro; cyano and aralkyl.

6. The compound of claim 1, wherein A is phenyl substituted by 1 to 3 substituents selected from the group consisting of lower alkyl and lower alkoxy.

7. The compound of claim 1, wherein X is lower alkylene having 2 to 4 carbon atoms, which is optionally substituted.

8. The compound of claim 7, wherein said lower alkylene is optionally substituted by amino, monoalkylamino, dialkylamino, carboxyl or lower alkoxycarbonyl.

9. The compound of claim 1, wherein X is a divalent residue of an aromatic compound, which is phenylene or naphthylene.

10. The compound of claim 1, wherein Y is a single bond.

11. The compound of claim 1, wherein Y is $C_1$-$C_8$ alkylene.

12. The compound of claim 1, wherein Z is a divalent residue of benzene which is optionally substituted.

13. The compound of claim 6, wherein A is trimethoxyphenyl, chlorophenyl or t-butylphenyl.

14. The compound of claim 1, wherein Z is —(CH=CH)$_2$—.

15. The compound of claim 11, wherein Y is —CH$_2$—.

16. The compound of claim 1, which is a salt.

17. The (compound of claim 16, which salt is a pharmaceutically acceptable salt.

18. The compound of claim 1, which is a solvate.

19. A pharmaceutical composition, comprising:

a) one or more compounds of claim 1; and b) a pharmaceutically acceptable carrier.

20. A method of treating an allergic immunological disease in a mammal, which comprises administering one or more compounds of claim 1, to a mammal in need thereof.

21. The method of claim 20, wherein said mammal is a human.

22. A method of treating asthma, atopic dermatitis, allergic rhinitis, inflammatory large bowel disease, contact dermatitis or allergic ophthalmopathy in a mammal, which comprises administering one or more compounds of claim 1, to a mammal in need thereof.

23. The method of claim 22, wherein said mammal is a human.

* * * * *

UNITED STATES PATENT AND TRADEMARK OFFICE
CERTIFICATE OF CORRECTION

PATENT NO.    : 6,448,242 B1  
DATED         : September 10, 2002  
INVENTOR(S)   : Hiroyuki Ishiwata et al.

It is certified that error appears in the above-identified patent and that said Letters Patent is hereby corrected as shown below:

<u>Column 65,</u>
Line 12, delete "(" between "by" and "one"

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,448,242 B1
DATED        : Sepetember 10, 2002
INVENTOR(S)  : Hiroyuki Ishiwata et al.

It is certified that error appears in the above-identified patent and that said Letters Patent is hereby corrected as shown below:

Column 65,
Line 11, "substituted by (one or more" should read -- substituted by one or more --.
Line 36, "piperizine or homopiperizine" should read -- piperazine or homopiperazine --.

Signed and Sealed this

Second Day of September, 2003

JAMES E. ROGAN
*Director of the United States Patent and Trademark Office*